United States Patent [19]

Hoenninger, III et al.

[11] Patent Number: 4,599,565

[45] Date of Patent: * Jul. 8, 1986

[54] METHOD AND APPARATUS FOR RAPID NMR IMAGING USING MULTI-DIMENSIONAL RECONSTRUCTION TECHNIQUES

[75] Inventors: John C. Hoenninger, III, Oakland; Lawrence E. Crooks, Richmond; Mitsuaki Arakawa, San Mateo; Jerome R. Singer, Berkeley, all of Calif.

[73] Assignee: The Regents of the University of Calif., Berkeley, Calif.

[ * ] Notice: The portion of the term of this patent subsequent to Oct. 27, 1998 has been disclaimed.

[21] Appl. No.: 515,117

[22] Filed: Jul. 19, 1983

Related U.S. Application Data

[63] Continuation-in-part of Ser. No. 331,008, Dec. 15, 1981, which is a continuation-in-part of Ser. No. 120,875, Feb. 12, 1980, Pat. No. 4,318,043, which is a continuation-in-part of Ser. No. 926,571, Jul. 20, 1978, Pat. No. 4,297,637.

[51] Int. Cl.⁴ ........................................... G01N 27/00
[52] U.S. Cl. ................................................. 324/309
[58] Field of Search ............... 324/300, 309, 311, 313, 324/312, 314

[56] References Cited

U.S. PATENT DOCUMENTS

| | | | |
|---|---|---|---|
| 4,070,611 | 1/1978 | Ernst | 324/309 |
| 4,115,730 | 9/1978 | Mansfield | 324/309 |
| 4,318,043 | 3/1982 | Crooks | 324/309 |
| 4,322,684 | 3/1982 | Hounsfield | 324/309 |

FOREIGN PATENT DOCUMENTS

| | | |
|---|---|---|
| 81/02789 | 10/1981 | PCT Int'l Appl. . |
| 81/02788 | 10/1981 | PCT Int'l Appl. . |
| 1310410 | 3/1973 | United Kingdom . |
| 1496886 | 1/1978 | United Kingdom . |
| 1580787 | 12/1980 | United Kingdom . |
| 2052753 | 1/1981 | United Kingdom . |
| 2057142 | 3/1981 | United Kingdom . |
| 1596160 | 8/1981 | United Kingdom . |
| 2091884 | 8/1982 | United Kingdom . |
| 1601816 | 11/1984 | United Kingdom . |

OTHER PUBLICATIONS

J. Phip. E: Sci. Instrum, vol. 13, (1980), pp. 697–707, "Automation and Control in High Power Pulsed NMR" by Geiger et al.
J. Mag. Nes. 29 (1978) 355–73 (particularly 363–7), "Biological and Medical Imaging by NMR" by Mansfield et al.
Phip. Rev. 94(4) (1/5/54) 630–8 (see FIG. 6), "Effects of Diffusion on Free Precession in Nuclear Magnetic Resonance Experiments" by Carr et al.

(List continued on next page.)

Primary Examiner—Stewart J. Levy
Assistant Examiner—Robert R. Raevis
Attorney, Agent, or Firm—Cushman, Darby & Cushman

[57] ABSTRACT

An imaging NMR scanner generates multi-dimensional NMR spin echo responses from selected sub-volumes of an object. 90° and 180° r.f. nutation pulses are used together with a variable amplitude gradient between these nutation pulses to phase encode a second dimension in the spin echo response which is already phase-encoded in a first dimension by use of a magnetic gradient during signal readout. Two-dimensional Fourier transforms or multiple angle projection reconstruction processes are then used to generate an array of pixel value data signals representing a visual image of the point-by-point spatial distribution of nutated nuclei within the object. Image artifacts potentially caused by relatively moving elements of the object are avoided by selecting the spin echo generating sub-volumes to avoid the moving elements. High resolution images of sub-volumes of interest can be obtained by selection of a sub-volume of interest in conjunction with these reconstruction techniques. Solutions for possible aliasing artifacts are also presented as are three-dimensional reconstruction techniques using NMR spin echo responses from such selected sub-volumes.

36 Claims, 28 Drawing Figures

OTHER PUBLICATIONS

J. Mag. Res. 33 83–106 (1979), "Sensitivity and Performance Time in NMR Imaging" by Brunner et al.
Letters to the Edition, May 12, 1980, "Spin Wrap NMR Imaging and Applications to Human Whole-Body Imaging" by Edelstein et al.
Abstract for 22nd Experimental NMR Conference Apr. 5–9, 1981, "In Vivo Comparison of Line Scan and Two Dimensional FT Imaging" by Crooks.
AJR: 137, Nov. 1981, pp. 895–901, "Magnetic Resonance Properties of Hydrogen: Imaging the Posterior Fossa" by Young et al.
J. Couput, Assist, Tomograph., vol. 6, No. 1982, "Initial Clinical Evaluation of a Whole Body Nuclear Magnetic Resonance (NMR) Tomograph" by Young et al.
Rev. Sci. Instrum., 53(a), Sep. 1982, "NMR Imaging Techniques and Applications: Review" by Bottomley.
Radiology, vol. 143, No. 1, pp. 169–174, Apr. 1982, "Nuclear Magnetic Resonance Whole Body Imager Operating at 3.5 K Gauss" by Crooks, et al.
"NMR Tomograph" by Bradley, 1982.

1, 2 ———
1', 2' - - -

EXEMPLARY GRADIENT/RF PULSE
SEQUENCE FOR PLANAR IMAGING
USING RECONSTRUCTION FROM
MULTIPLE ANGLE ONE-DIMENSIONAL
PROJECTIONS

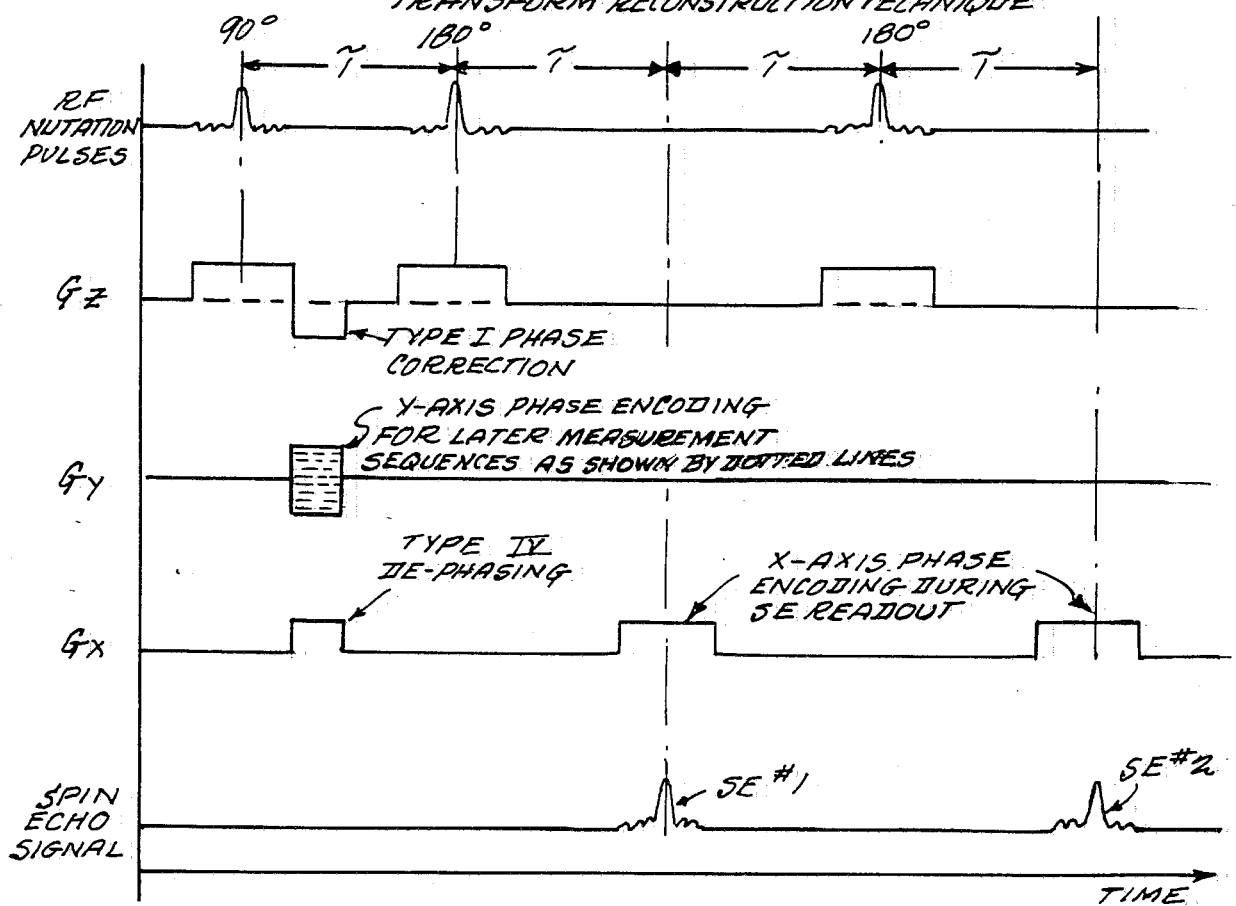
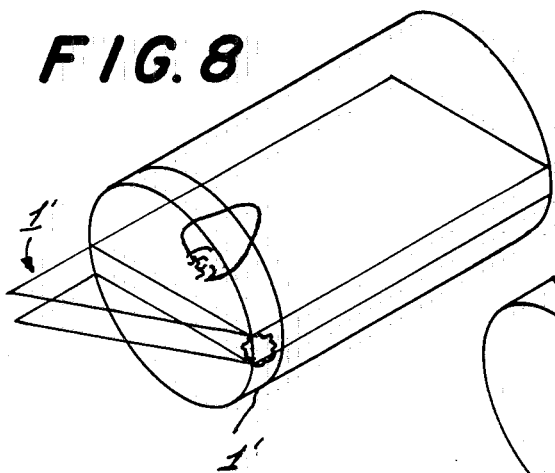
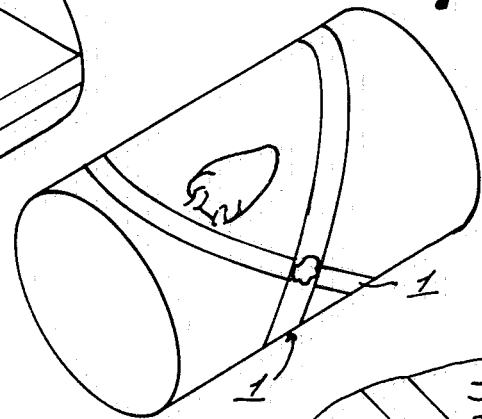
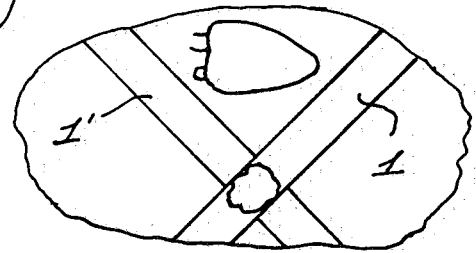

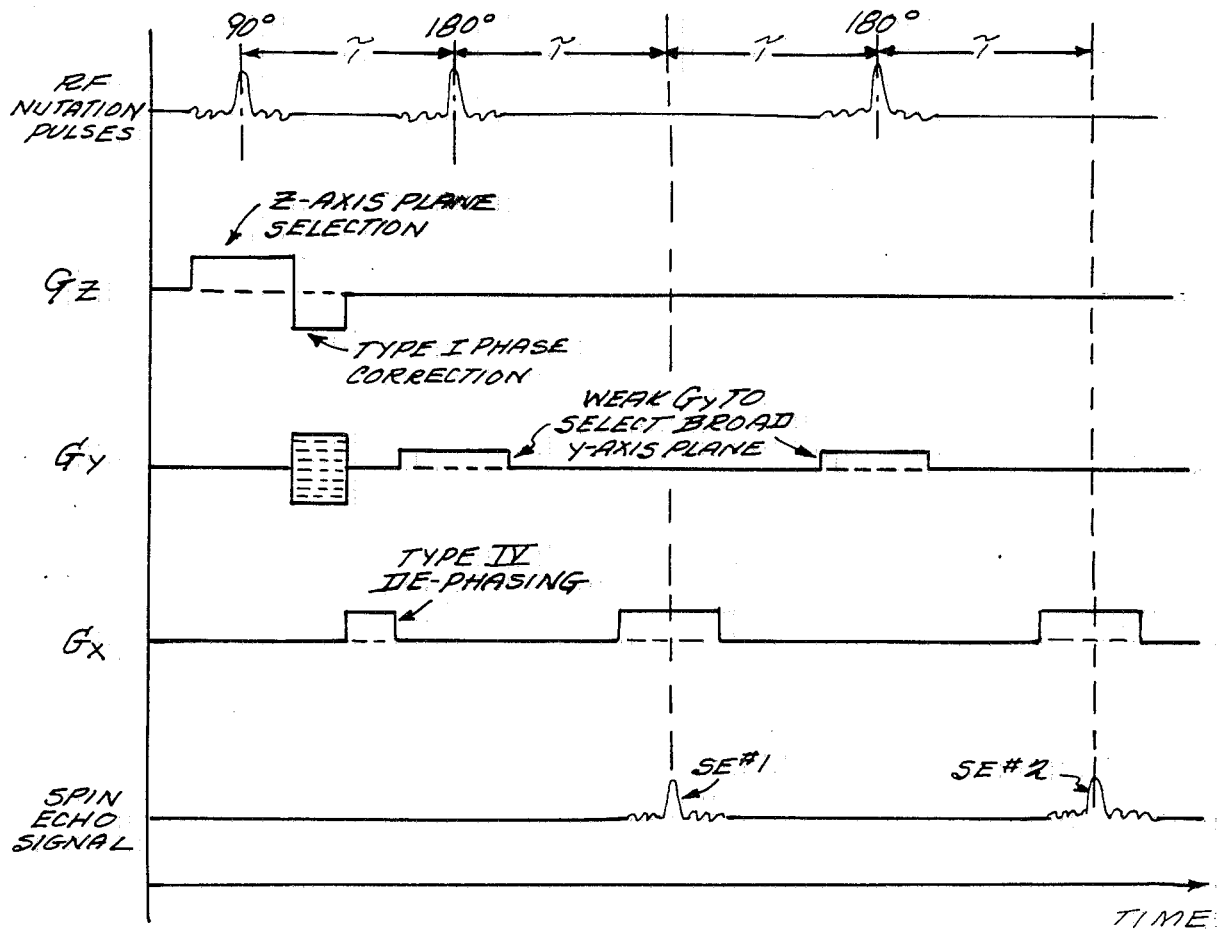

FIG. 13a
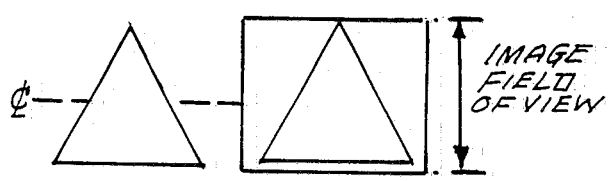
FIG.13b
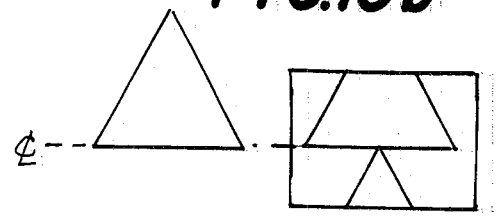
FIG. 13c
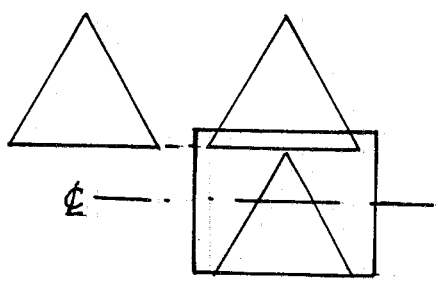
FIG.13d
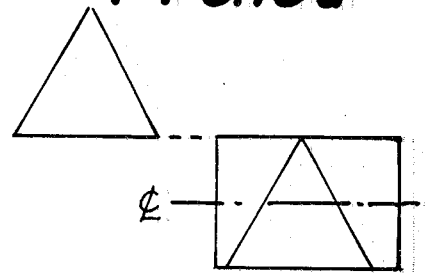
FIG.13e
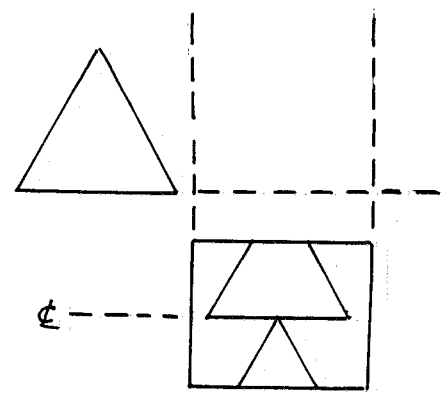
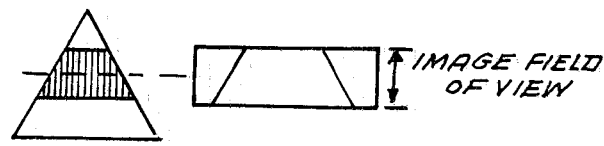
FIG. 14a
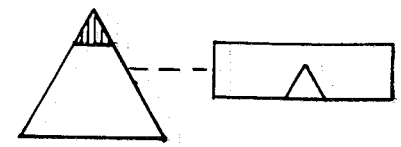
FIG.14b
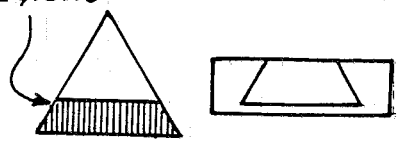
FIG. 14c

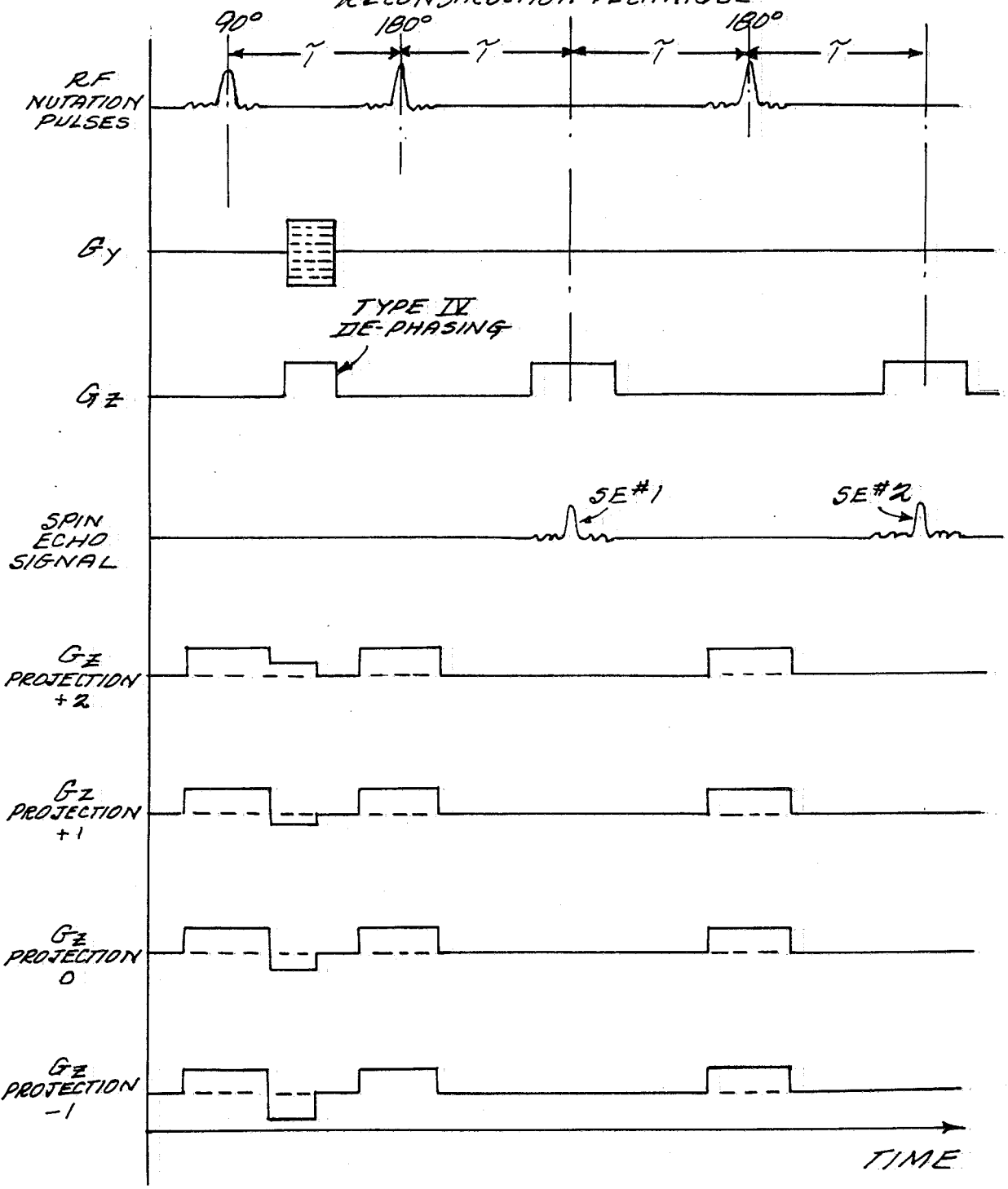

TWO-DIMENSIONAL MULTIPLE ANGLE PROJECTION RECONSTRUCTION TECHNIQUE

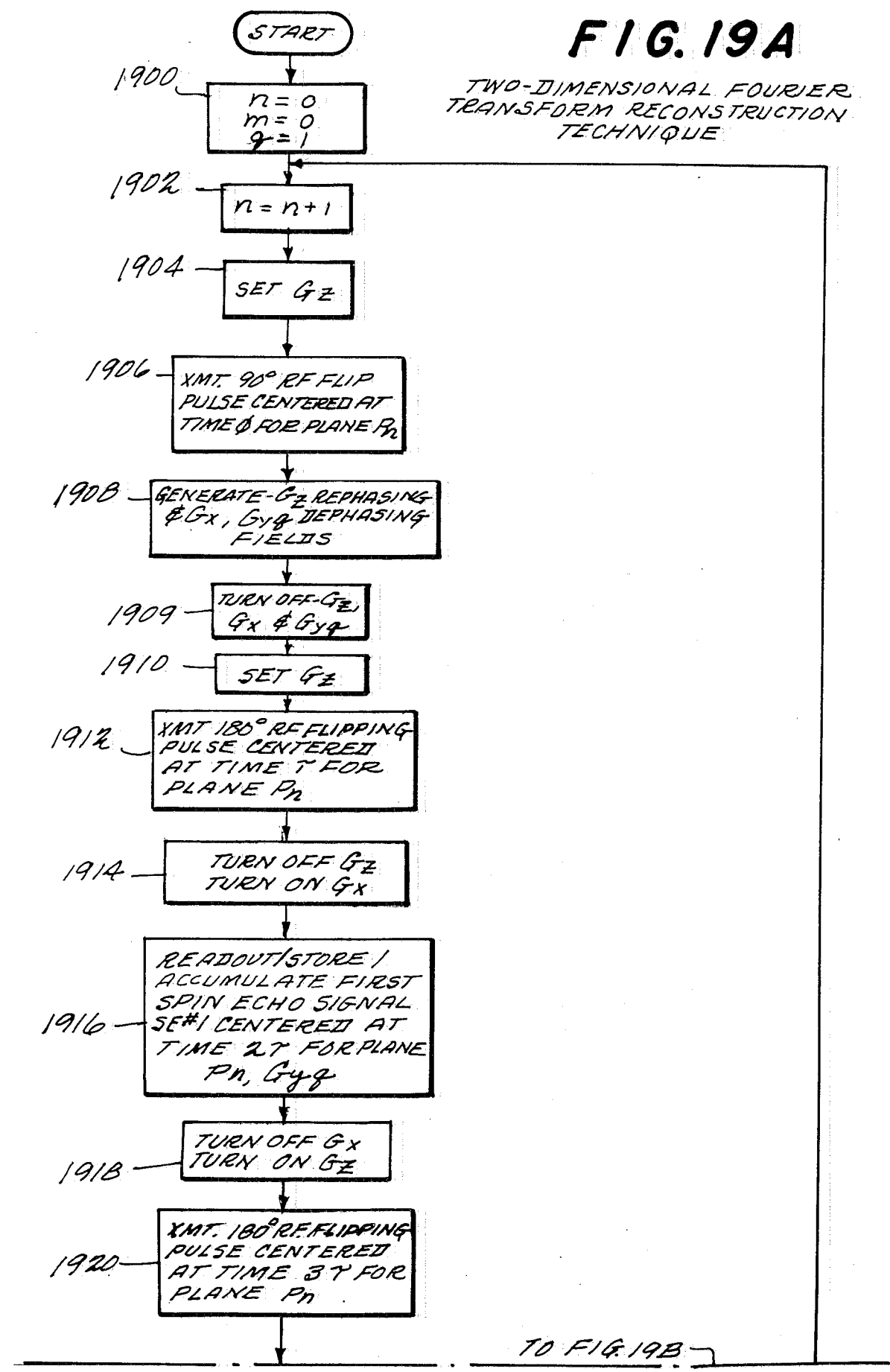

METHOD AND APPARATUS FOR RAPID NMR IMAGING USING MULTI-DIMENSIONAL RECONSTRUCTION TECHNIQUES

This application is a continuation-in-part of our earlier copending, our commonly assigned application Ser. No. 331,008, filed Dec. 15, 1981 which is, in turn, a continuation-in-part of our commonly assigned application Ser. No. 120,875, filed Feb. 12, 1980 (now U.S. Pat. No. 4,318,043) which is, in turn, a continuation-in-part of commonly assigned application Ser. No. 926,571, filed July 20, 1978 (now U.S. Pat. No. 4,297,637). The entire specifications and drawings of this earlier related copending application and of these earlier related now issued U.S. patents are hereby expressly incorporated by reference.

This invention relates to apparatus and method for NMR (nuclear magnetic resonance) imaging wherein data representing the internal point-by-point distribution of selected molecular structures within an object under test is obtained using nuclear magnetic resonance phenomena.

NMR imaging is based on the ability to induce and monitor resonance of the magnetic moment of selected nuclei in the presence of magnetic fields. By the use of position-variant magnetic fields, it is possible to measure both the location and concentration in small volumes of resonant nuclei and, thereby, to create a visual display image that reflects this distribution in living tissue (e.g., a human body) or in other internal structures of an object under examination. Hydrogen, because it is the most sensitive of the stable nuclei to NMR phenomena and because it is also the most abundant nucleus in the human body, is ideally suited for NMR imaging. NMR imaging is a non-invasive diagnostic technique having some general similarity to computed tomography scanning (utilizing X-ray radiation) albeit it is based upon an entirely different physical phenomenon.

A detailed explanation of the particular NMR spin echo phenomena is already set forth in our related earlier referenced copending application and issued patents. Nevertheless, a brief review of some salient points is included here.

The instrumentation for NMR imaging systems reflects the sequence by which nuclear magnetic resonance is achieved. A typical system will include a large magnet to create the surrounding magnetic field, magnetic field gradient producing coils to create position dependent magnetic fields, an RF coil to apply and receive the resonant frequency r.f. signals, electronic circuitry to generate, transmit and record the electromagnetic radiations, and a digital data acquisition, processing, and display system.

A variety of different NMR methods to define a measured volume have been developed. All techniques, however, are based on the relationship between RF frequency and magnetic field. Because it is impossible to create a magnetic field with a different strength at every point in space at the same time, all techniques use changing magnetic fields to define volumes. Magnetic field gradients can be used during transmission or reception or both.

The exemplary NMR imager described in our earlier-referenced application and patents illustrates electronic selection of line volumes in the object. A slice in the sample can be excited by exposing the sample to a magnetic field variation and an r.f. magnetic field such that only the desired plane corresponds to the frequencies of the r.f. magnetic field. Two intersecting such planes can be excited and the two r.f. fields which separately excite the planes can be chosen so that a signal known as a spin echo will be emitted (at a later time) by only the nuclei at the intersection of the two excited planes. If the planes are both thin and substantially perpendicular to one another, then a "line volume" can be defined by their intersection. The spin echo under these circumstances contains information about only the nuclei within this common intersecting line-volume. By applying a field variation along such a line, for example, during read out, a frequency discrimination of the emitted r.f. signal is produced along that line. The intensity I of each frequency of the spin echo will be a function of the hydrogen density H, the T1, and T2 parameters of a volume element along the selected line. A map of the hydrogen density modified by T1 and T2 can thus be obtained from the frequency spectrum of the spin echo signal. The relaxation times can be measured by observing signal strength when the relevant T1 and T2 instrument parameters are varied.

In NMR imaging, the signal-to-noise ratio (S/N) in the instrument is dependent on a variety of factors including the strength of the magnetic field, the resolution volume, the total volume of the system, the imaging technique being used, and the imaging time. However, it is important to realize that the value of S/N in the instrument is not equivalent to S/N in the final image. This latter parameter depends on a number of factors. For instance, it depends on both the chosen spatial resolution and on imaging time. The spatial resolution is given by the volume from which signals will be received. Since noise is determined mostly by the instrument, larger volumes produce larger signals and improved S/N. On the other hand, as the size of the resolution volume increases with respect to object size, blurring will decrease contrast in the output image in a predictable manner. Thus, when imaging a small object, a relatively large resolution volume (although it would increase the S/N for the instrument) would have an adverse effect on the S/N of the output image.

Longer imaging times result from using a larger number of signal accumulations in the image formation process (e.g. the combination of more spin echos before Fourier transformations or other reconstruction processes are performed). The larger number of data sets thus obtained allow for more accurate averaging of the data. Object motion, though, can negate this advantage.

In general, the signal-to-noise ratio, S/N, for the instrument can be written as $$S/N = sVt^{\frac{1}{2}} = sXYZt^{\frac{1}{2}} \quad \text{(Equation 1)}$$

where s is a constant that represents the sensitivity of the system, V is the resolution element volume, equal to the product of its dimensions X, Y, & Z, and t is the imaging time. The volume term arises from the linear relationship between the number of hydrogen nuclei resonating (i.e., providing signal) in the region of a homogeneous object and the volume of that region. The $t^{\frac{1}{2}}$ term arises from the nature of the noise, which is presumed to be pure "white" noise produced by the electronics, and is consequently averaged to zero as more averages are used resulting in longer measuring periods. Coherent noise, for instance, picked up from a computer clock, will affect the image in a manner not susceptible to elimination through averaging. The term s is a function of the value of the polarizing magnetic field.

Our earlier illustrative line-by-line NMR imaging techniques obtained NMR spin echo responses from intersecting sub-volumes or regions of an object which were sequentially and selectively irradiated respectively by 90° and 180° r.f. nutation pulses. The intersecting sub-volume giving rise to the spin echo NMR responses was then moved through the portion of an object to be imaged by changing the frequencies of the r.f. pulses used to select such intersecting sub-volumes for successive measurement cycles. Once the magnetization of the nuclear spins in the portions of the object excited by either the 90° or 180° nutation pulses was thus disturbed, it had to be allowed to return towards an equilibrium condition for a time on the order of T1.

Since the time required to produce and record one or more NMR spin echo signals obtained during a given measurement cycle in a selected sub-volume is short compared to T1 (spin echo recording times are typically less than 100 milliseconds while T1 is typically on the order of 1,000 milliseconds), the effective duty cycle of the image data gathering activities might initially appear to be quite low using our 90° and 180° r.f. nutation pulse technique to select sub-volumes of the object for NMR responses. However, as described in more detail in our previous issued patents and/or copending patent application, an additional improvement in the effective duty cycle can be realized by proceeding to excite and record additional sub-volume regions (selected from the volumes not affected by previous r.f. nutation pulses) during the time required for recovery of a given region after eliciting an NMR spin echo response therefrom. In effect, the data gathering activities for a plurality of different regions (e.g., planar volumes or "slices") are interleaved in a time/spatial division multiplexing technique. As explained in our earlier patents and/or application, one can continue this time/spatial division multiplexing process to acquire signals from a "diagonal" set of regions defining a single planar volume or "slice". In general, this rapid multiple plane imaging process greatly increases the effective data gathering duty cycle of our NMR imaging process.

Although this rapid time/spatial division multiplexing technique can be applied generally to subvolumes other than line volumes, the exemplary illustrative embodiments described in our earlier issued patents and/or pending application primarily focus upon obtaining NMR spin echo responses from line volumes.

However, theoretical considerations indicate that generating data from a relatively small line volume is less efficient in some respects (e.g., a lower signal-to-noise ratio) than other techniques for imaging the same line volume but using reconstruction techniques which extract the point-by-point spatial distribution of nutated nuclei therealong from NMR response data emanating from a larger signal-generating volume (e.g., using multiple angle one-dimensional density projections through the region of interest). See, for example, the discussion by P. Brunner and R. R. Ernst entitled "Sensitivity and Performance Time in NMR Imaging" in the Journal of Magnetic Resonance, 33, 83–106 (1979).

We have now experimentally verified such theoretical considerations as reported by L. E. Crooks "In Vivo Comparison of Line Scan and Two-Dimensional FT Imaging" at the 22 Annual Experimental NMR Spectroscopy Conference, Asilomar, Calif., Apr. 5–9, 1981.

In conjunction with a non-printed presentation, a brief printed abstract was published stating as follows:

> "NMR images are presented based on a line scan technique using spin echoes and a two-dimensional FT also using spin echoes. The signal-to-noise performance of the two techniques is compared for a uniform phantom. Image time and resolution are made the same for both techniques. The response to object motion is compared using a hot spot phantom."
>
> "Signal-to-noise and motion sensitivity are compard for images through the chest and abdomen of a live rat. T1 and T2 images are also presented for both techniques."

As might be expected from this abstract, the oral presentation focused upon a comparison of experimental results rather than on the specifics of implementing the two different imaging techniques being compared. However, a visual chart generally conforming to a portion of FIG. 7 herein was briefly exhibited and discussed at this meeting. The exhibited chart showed the gradient/r.f. pulse sequence of FIG. 7 only through the first 180° r.f. nutation pulse and did not include the detailed explanatory notations now included in FIG. 7 of this application. Other than the fact that a two-dimensional Fourier transform reconstruction technique using spin echo data was said to have been employed to achieve the compared results, there was no detailed discussion of the actual reconstruction technique implemented.

We have discovered that our technique of eliciting NMR spin echo signal responses from selected sub-volumes of the object under test (e.g., using a sequence of 90° and 180° r.f. nutation pulses) so as to localize the NMR signal producing regions can be advantageously combined with two- and/or three-dimensional reconstruction processes when the selected spin echo producing region is made larger than a simple line volume.

For example, if a common planar volume or slice is selected by both the 90° r.f. nutation pulse and the 180° r.f. nutation pulse, the resulting spin echo signal will be generated from the entire volume. A one-dimensional projection of the nuclear spin densities through this selected volume can then be obtained by a first Fourier transformation of the spin echo signal (or of an accumulated average of several similar such spin echo signals). If several such one-dimensional projections are taken at different angular orientations, then conventional multiple angle projection reconstruction processes can be utilized to reconstruct the spatial point-by-point density distribution of the nutated nuclei throughout the selected plane (e.g., using conventional convolution/back projection techniques as employed in computed X-ray or other tomography techniques). Alternatively, a plurality of such one-dimensional projections may be obtained at one angular orientation but with different transverse level phase encoding corresponding to different spatial levels within the selected volume. A second dimensional Fourier transformation may be made across such different levels in the first resulting array of projected density data values so as to thus deduce the point-by-point spatial distribution of nutated nuclear densities throughout the selected volume.

By selectively irradiating at a given time only a single planar volume with the 90° and 180° nutation pulses, a rapid multiple plane imaging process (i.e., the above-mentioned time/spatial division multiplex during a T1 relaxation time) can also still be realized. Furthermore, since the 90° and 180° nutation pulses selectively excite a common plane, there is no expected interference due to a residual FID from areas selected by the 90° nutation pulse but not by the 180° nutation pulse—as is the case for line-by-line imaging. Thus, the need for repeating particular sequences of four differently phased r.f. pulses together with a specific arithmetic accumulation of the resulting four NMR spin echo responses so as to cancel the residual FID interference (as explained in our above-referenced copending application) may be avoided. However, this particular sequence of phased r.f. nutation pulses and accumulation of resulting spin echo signals would still offer advantages if the 90° and 180° r.f. nutation pulses do not select exactly the same planar volume. And, if the spatial sequence of four phased r.f. nutation pulses and resulting spin echos are not used or required, the number of individual spin echo signals that are accumulated and averaged together may be reduced, if desired, for particular applications.

Prior two-dimensional Fourier transform NMR imaging techniques (sometimes referred to as "spin warp imaging") preprocess the object with the adiabatic fast passage of an 180° r.f. inverting pulse—which substantially prevents the use of rapid multiple plane imaging techniques using the time/spatial division multiplex techniques mentioned above. Typical prior art spin warp imaging techniques are disclosed by Edelstein et al, "Spin Warp NMR Imaging and Applications to Human Whole-Body Imaging", Physics in Medicine and Biology, 25(4), 751–756 (1980) and Hutchison et al, PCT International Patent Application No. PCT/GB81/00044 dated Mar. 14, 1980 (publication No. WO81/02788).

Such prior art "spin warp imaging" typically produces the "spin echo" by reversing the magnetic gradient in the X direction so as to cause controlled de-phasing of the nuclei followed by a subsequent re-phasing X direction magnetic gradient. However, by following our spin echo imaging technique (which utilizes a 180° r.f. nutation pulse affecting only a sub-volume of interest to re-phase the spins), another considerable advantage is achieved. For example, any de-phasing of the nuclear spins caused by magnetic field inhomogeneity is substantially eliminated because the 180° r.f. nutation pulse inherently cancels any such de-phasing effects.

At the same time, the use of a 180° r.f. nutation pulse to produce the spin echo response permits additional 180° r.f. nutation pulses to be used thereafter so as to obtain additional spin echo NMR signal responses from the volume of interest. Each of these successive spin echo signals can itself be used to produce an image and/or, at least two such successive spin echo images can be utilized to calculate a T2 image without the necessity of undergoing a completely separate measurement cycle (so as to get another point on the T2 exponential curve for each image point). This latter feature and ability is further explained in our above-referenced copending patent application.

Although the prior "spin warp imaging" techniques can also obtain successive spin echo signals by continuing to alternate the X gradient (and thus increase the T2 dependence and possibly permit one to calculate T2 images), such successive spin echo signals will possess progressively more distortions due to inherent induced errors from magnet inhomogeneity as discussed above.

Since the prior art spin warp imaging technique involves a sequence which merely requires reversal of a single magnetic gradient, it is probably possible to obtain the first spin echo signal in a given measurement cycle more quickly than in our technique (which requires switching off one gradient and switching on a second gradient, transmitting a 180° r.f. nutation pulse and then switching off the second gradient). The spin warp technique should theoretically have a somewhat higher signal-to-noise ratio although a lower T2-based contrast. However, as mentioned above, if one continues to alternate the gradient in the prior spin warp technique to get more spin echoes so as to increase the T2 dependence, progressively more distortion of the generated spin echo signals can be expected due to magnet inhomogeneity and the de-phasing problems caused by it.

Using our NMR imaging technique where spin echo signals are generated by 180° r.f. nutation pulses, it should be noted that each such 180° nutation pulse reverses the relative phase of the resulting spin echo signal. Accordingly, the induced phase encoding employed in the multi-dimensional NMR imaging techniques now presented in the present application (e.g., due to the Y-axis magnetic gradient) will be reversed in every other spin echo signal obtained in a given measurement cycle. The result is that if a corresponding succession of spin density images is created from respective ones of these successive spin echo signals, they will be reconstructed in a relatively upside down orientation. However, once the reconstructed data is available, it is a relatively simple matter for the data acquisition and reconstruction computer to reverse the order of each horizontal line of pixels stored in the computer memory from alternate ones of the spin echoes. Display of the images from the memory will show all spin echoes correctly right side up.

In general, planar imaging should produce a signal-to-noise ratio advantage of approximately the square root of N where N equals the number of projections used in the reconstruction process as compared to imaging the N lines one at a time using a line-by-line data collection and imaging process.

Many of the above-mentioned advantages continue to be present when other selected sub-volumes of the object (but greater than a simple line volume) are utilized for generating the NMR spin echo responses which are subsequently to be processed by a multi-dimensional reconstruction technique as earlier described. For example, a portion of a planar volume may be selectively excited to provide spin echo responses by the intersection of relatively thin and relatively thick sub-volumes by respective 90° and 180° nutation pulses. A suitable two-dimension reconstruction process as described above for imaging a complete planar volume can then be employed to image this selected portion of the planar volume. In this manner, one may directly collect NMR data from only the desired sub-region of interest in an object and therefore simplify the image reconstruction process. Another alternative would be to provide a first coarse resolution image of a large area so as to locate a suspected tissue or organ and to thereafter select a sub-region centered on the suspected tissue and concentrate on the actually desired region with a more highly resolved image. This permits one to concentrate a number of quite high resolution pixels on only a desired area of interest rather than being forced by sampling requirements to attempt coverage of the fully extended object cross-section with the many more pixels required by the desired high resolution.

If the just-discussed sub-region imaging technique is realized using the intersection of non-coextensive sub-volumes (one of which is excited by a 90° nutation pulse while the other is excited with a 180° nutation pulse so as to produce a spin echo only from their intersection), then interfering residual FID signals may well be present such that four phased variations of 90° and 180° nutation pulses are preferably used together with the coherent detection and accumulation of spin echo responses (as discussed in our earlier copending application) so as to minimize or eliminate such interfering residual FID signal components. Furthermore, the next selected sub-region that might be excited to produce a spin echo within the same T1 relaxation period would have to be chosen from a region not common to either of the earlier regions just excited by a 90° and/or 180° nutation pulse. Since these regions may well be outside the desired region of interest, there may be little point in imaging them. If one is not sure of the utility of these regions they can be included in the imaging at no cost in image time. They can be reconstructed and viewed. If they are in fact of interest they can be saved, if not the data can be discarded. The only cost of this approach is that computer storage is used for the additional data. If the data is usually discarded the effectiveness of the multiple rapid plane feature (i.e. the time/spatial division multiplex technique) may be effectively lost.

However, at the same time, there are potential compensating advantages. For example, one may reduce or substantially eliminate motion artifacts in the reconstructed images for at least some locations of a selected sub-region of interest. This is possible by choosing the excited regions (e.g., the selected plane excited by a 90° nutation pulse and the selected plane excited by a 180° nutation pulse which intersect in the region of interest) so as to avoid the relatively moving elements of the object (e.g., the beating heart of a human). This is but another advantage of exciting only selected sub-volumes of the object with 90° and 180° nutation pulses thus avoiding NMR signal responses which include signal components from outside the real area of interest.

One possible problem that may be encountered in utilizing a two-dimensional Fourier transform embodiment of the present invention is the appearance of aliasing in the vertical dimension (e.g., the dimension corresponding to the gradient axis used for phase encoding the second dimension). If the signal producing region is larger than the reconstructed field of view and/or if the horizontal centerline (i.e., the dimension transverse to the magnetic gradient used for phase encoding the second dimension) of the region of interest is not coincidentally aligned with the corresponding centerline of the reconstructed field of view aliasing problems can be expected. In the latter instance, the reconstructed image will be aliased about a field of view centered on the centerline of the phase encoding gradient field. This potential problem can be compensated by further signal processing in the image display controller (or elsewhere) so as to "unwrap" the horizontal lines of display pixel values in the actually displayed image.

The two-dimensional planar and sub-planar NMR image reconstruction techniques already discussed can also be extended to three dimensions. For example, another of the magnetic field gradients (e.g. Z axis) can be fixed at different values for different complete cycles of spin echo data taking. A succession of such data taking cycles with different Z-axis phase encoded spin echo signals in this further dimension permits a third dimension of Fourier transformation to result in a three-dimension point-by-point spatial distribution of the nutated nuclear densities.

These and other objects and advantages of this invention will be more completely understood and appreciated by reading the following detailed description of the presently preferred exemplary embodiments of this invention taken in conjunction with the accompanying drawings, of which:

FIG. 7 is a graph showing exemplary gradient/r.f. pulse sequences for planar imaging using two-dimensional Fourier transform reconstruction techniques;

FIG. 8 illustrates a situation where motion artifacts may be expected from relatively moving elements in the object under test;

FIG. 9 and FIG. 9a illustrate the same object under test and area of interest as in FIG. 8 but with the selected NMR-excited sub-volumes being chosen so as to avoid the relatively moving element of the object and thus avoid motion artifacts in the reconstructed image;

FIG. 11 is an exemplary gradient/r.f. pulse sequence similar to FIG. 7 but illustrating the selection of a sub-planar region of interest for a two-dimensional Fourier transform image reconstruction technique;

FIGS. 13a–13e illustrate a similar aliasing problem to be expected in the two-dimensional Fourier transform reconstruction embodiments of this invention where the horizontal centerline of the object under test is not aligned with the horizontal centerline of the reconstructed field of view;

Figure 17:
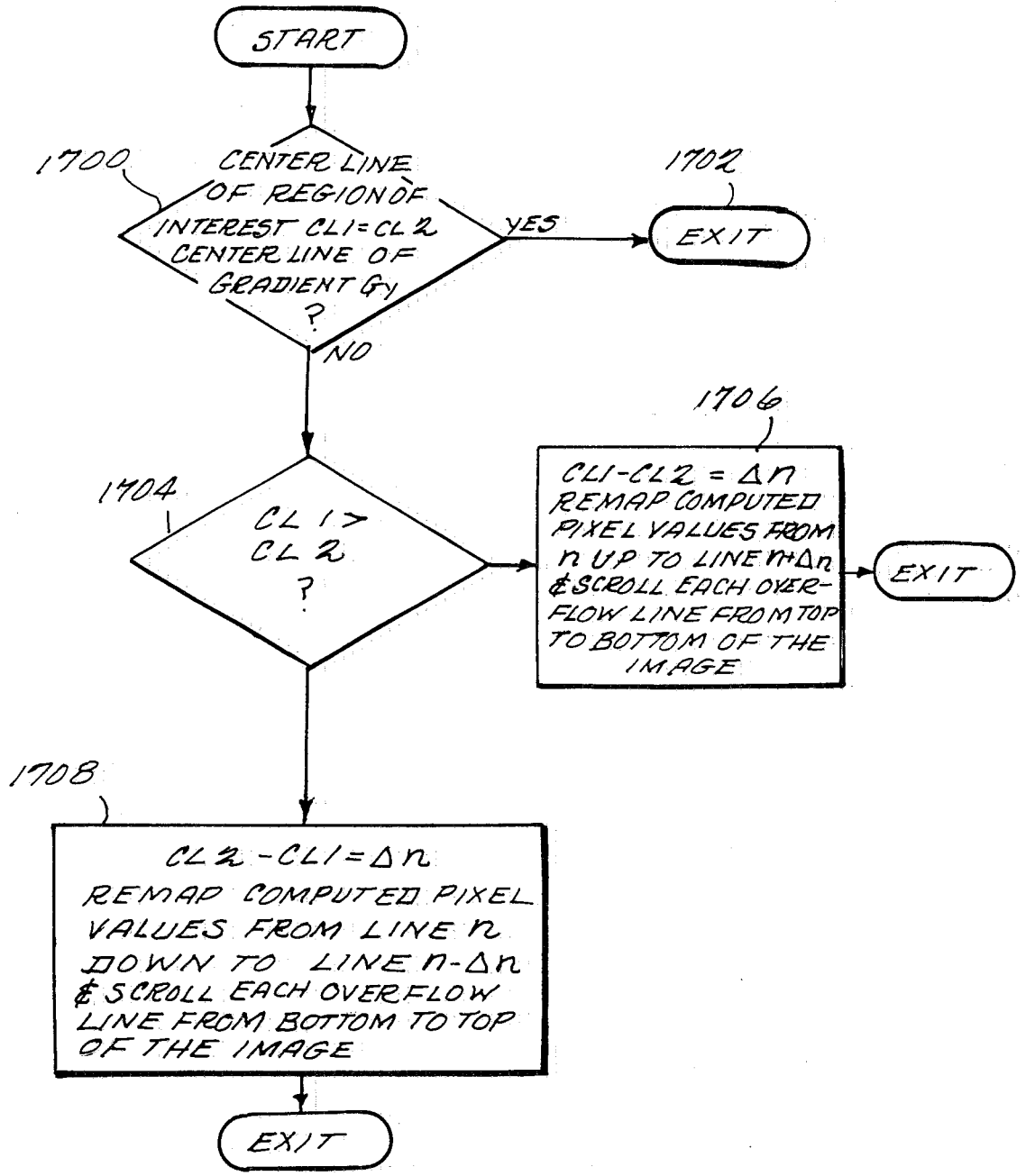
Figure 18A:
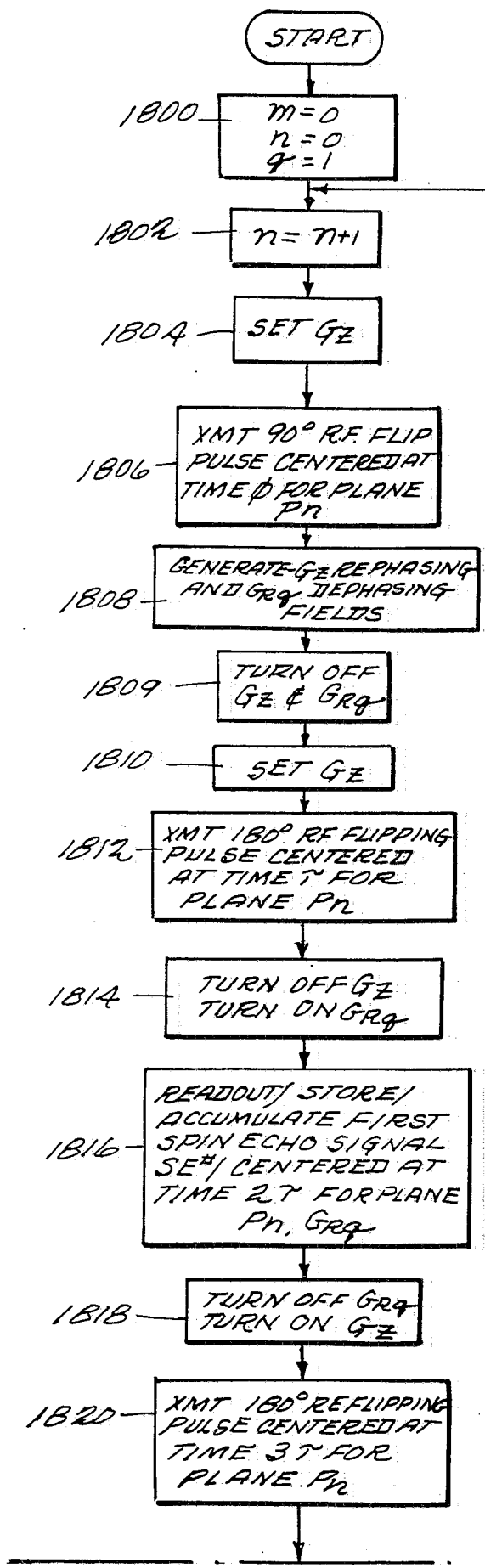
Figure 18B:
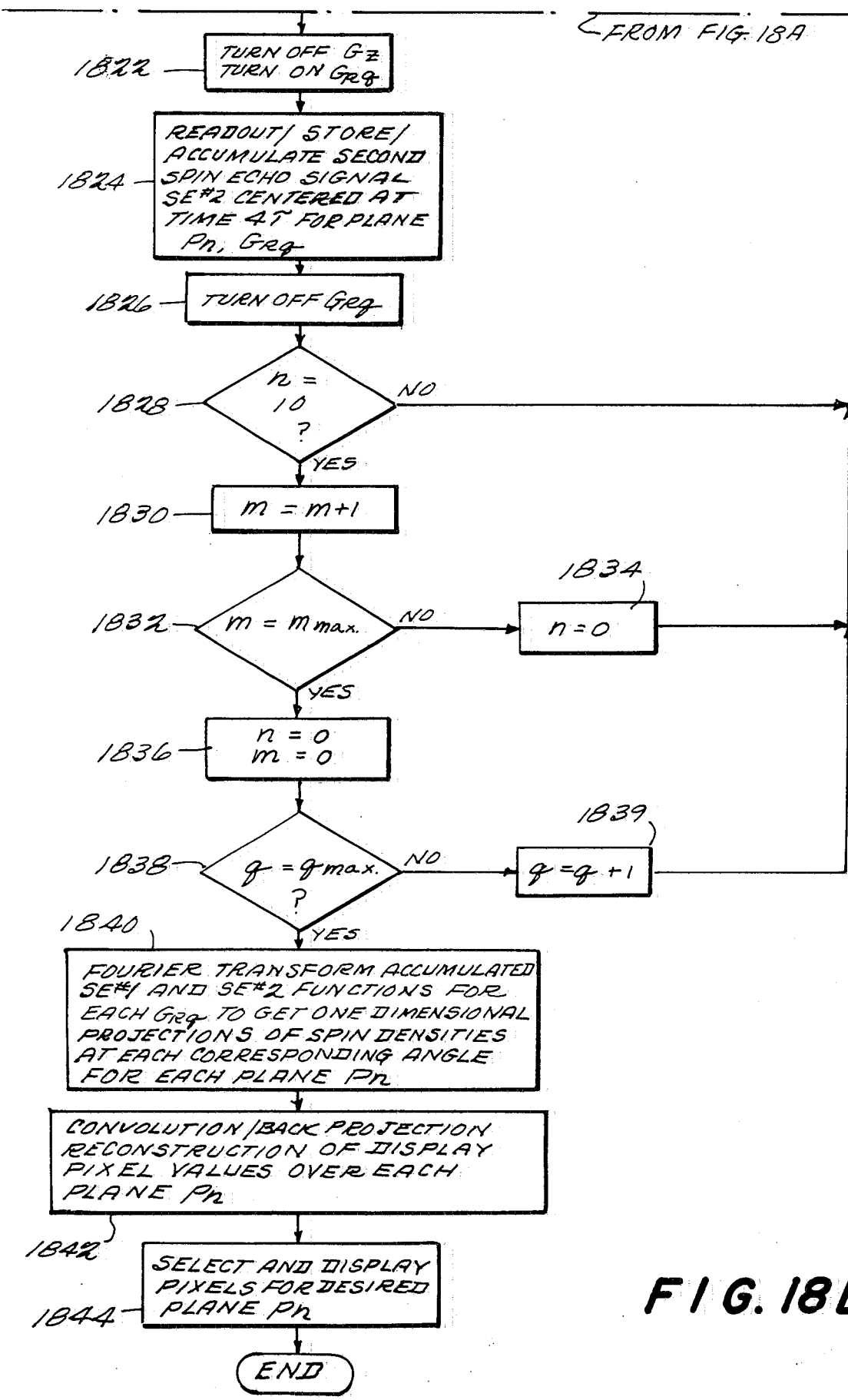
Figure 19B:
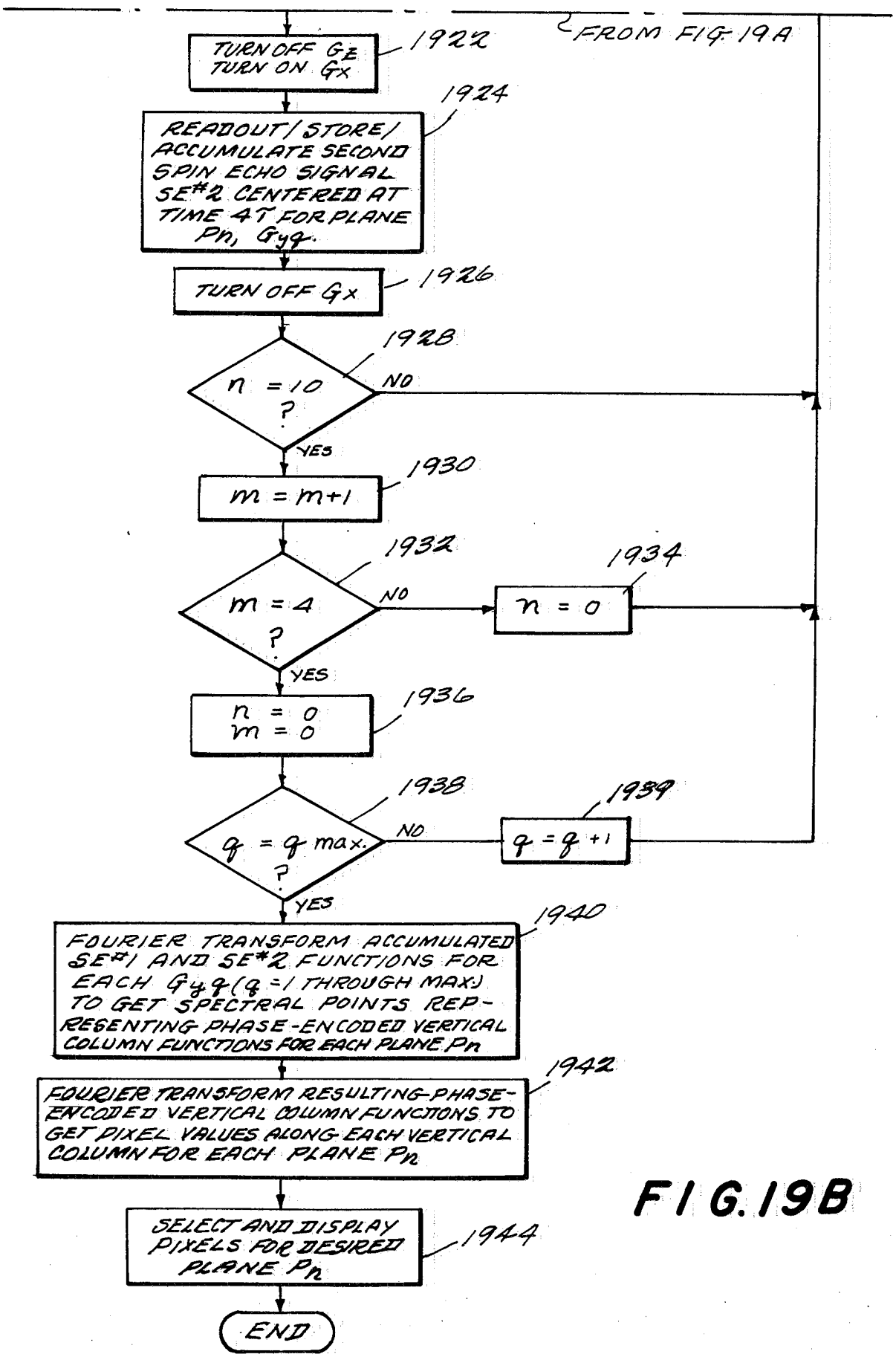

FIGS. 14(a)-14(c) illustrate a similar aliasing problem to be expected in the two-dimensional Fourier transform embodiment of this invention where the selected sub-volume or region of interest generating spin echoes has a horizontal centerline which is not aligned with the horizontal centerline of the reconstructed image field of view;

FIG. 15 schematically depicts the relatively thicker selected planar volume for providing spin echo signals when a three-dimensional Fourier transform reconstruction technique is employed;

FIG. 16 illustrates an exemplary gradient/r.f. pulse sequence for such three-dimensional imaging as is schematically depicted in FIG. 15;

FIG. 17 is an illustrative computer program flow chart for a program segment that may be used to compensate the expected aliasing problem to be encountered with some embodiments of this invention;

FIGS. 18A and 18B are illustrative computer program flow charts for generating, recording, reconstructing and displaying images of nuclear density within a selected sub-volume of an object under test using a two-dimensional multiple angle projection reconstruction technique; and FIGS. 19A and 19B are also an illustrative flow chart of a computer program which may be utilized in implementing this invention using two-dimensional Fourier transform reconstruction techniques.

Figure 1:
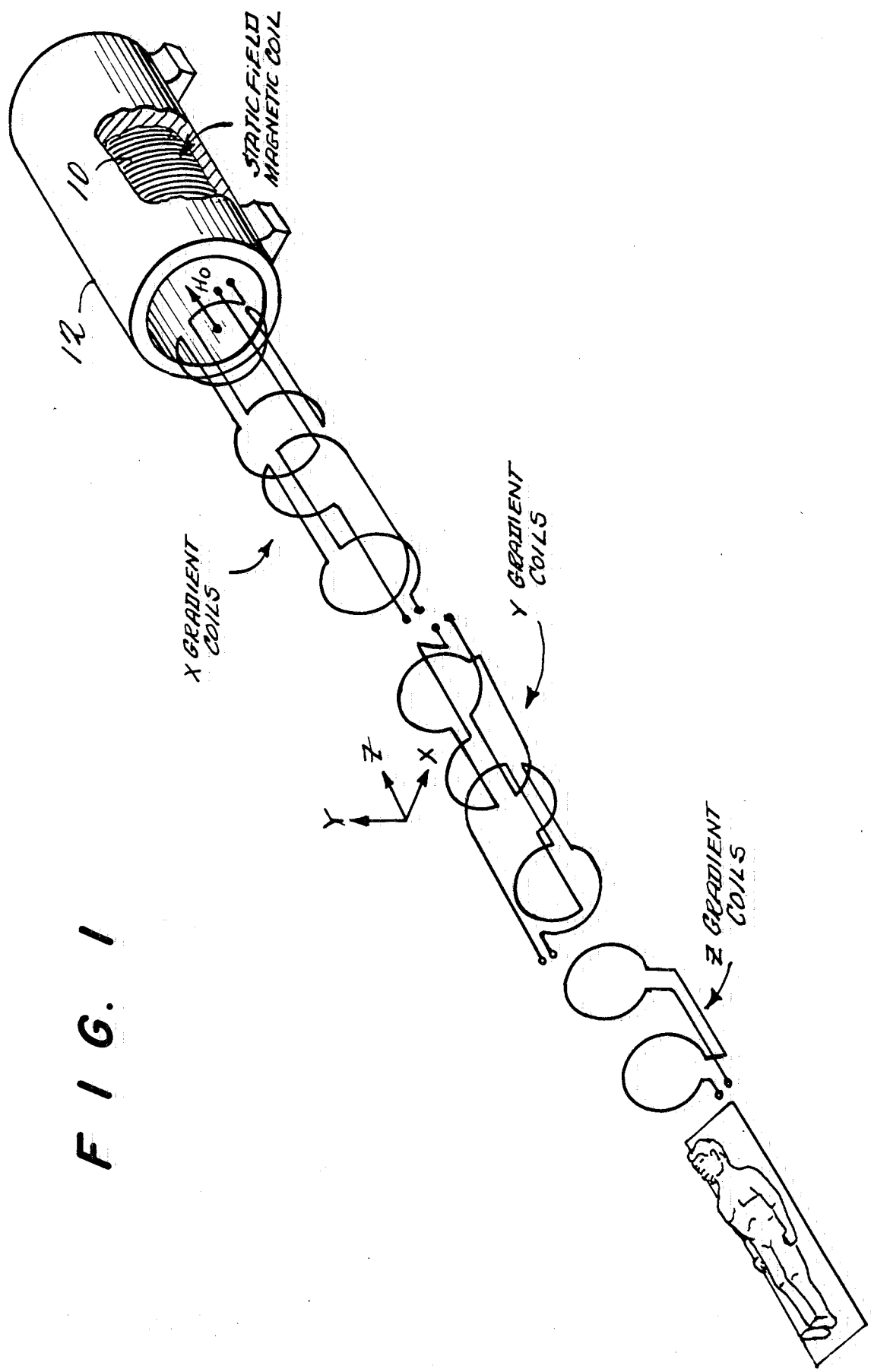
FIG. 1 is an exploded perspective view of a suitable static magnetic coil and gradient coils for use with an exemplary embodiment of this invention.
Figure 2:
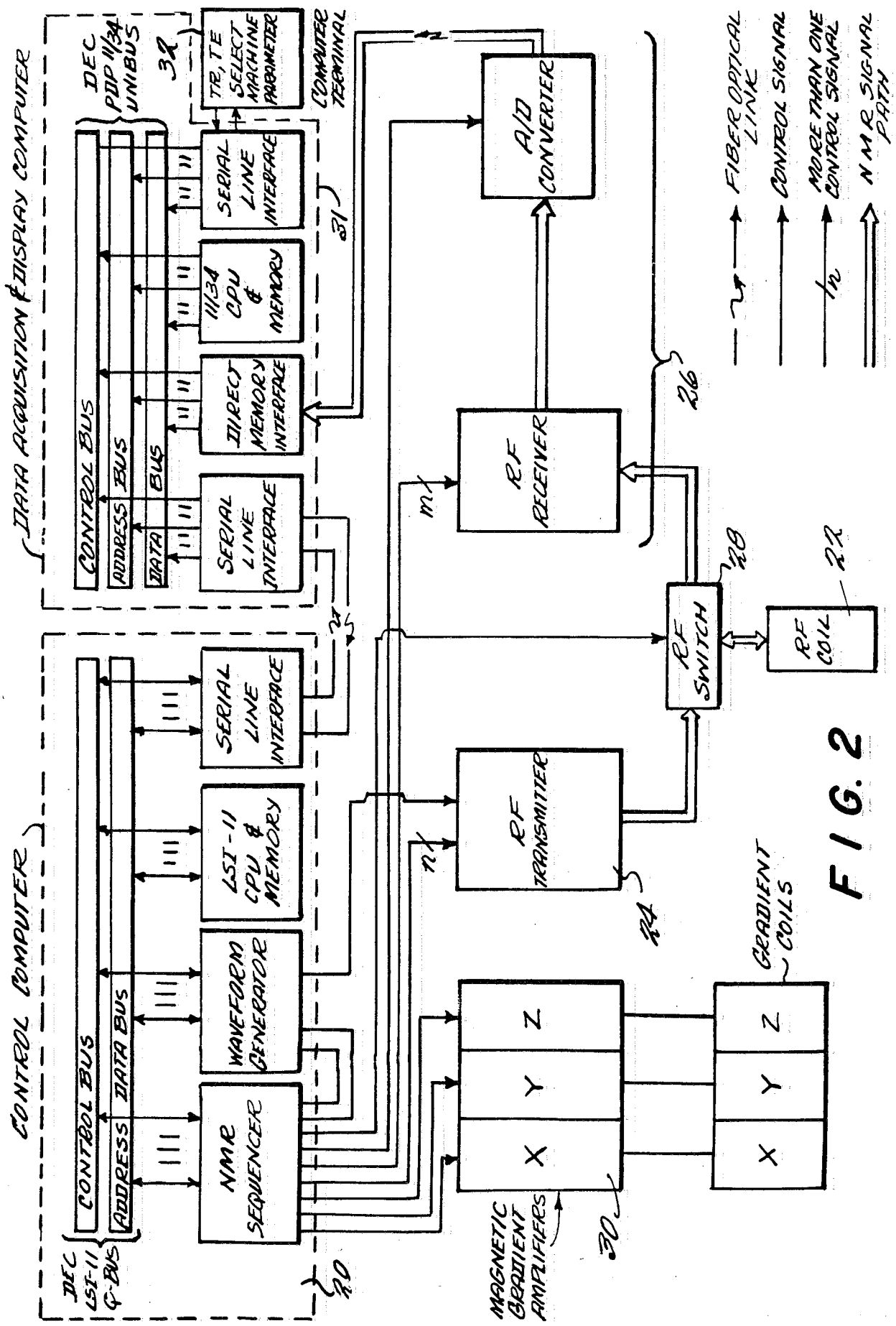
FIG. 2 is a block diagram of the computerized electronic apparatus utilized for driving the magnetic gradient coils and the r.f. circuits including a transmitting-/receiving r.f. coil for an exemplary embodiment of this invention.
Figure 3:
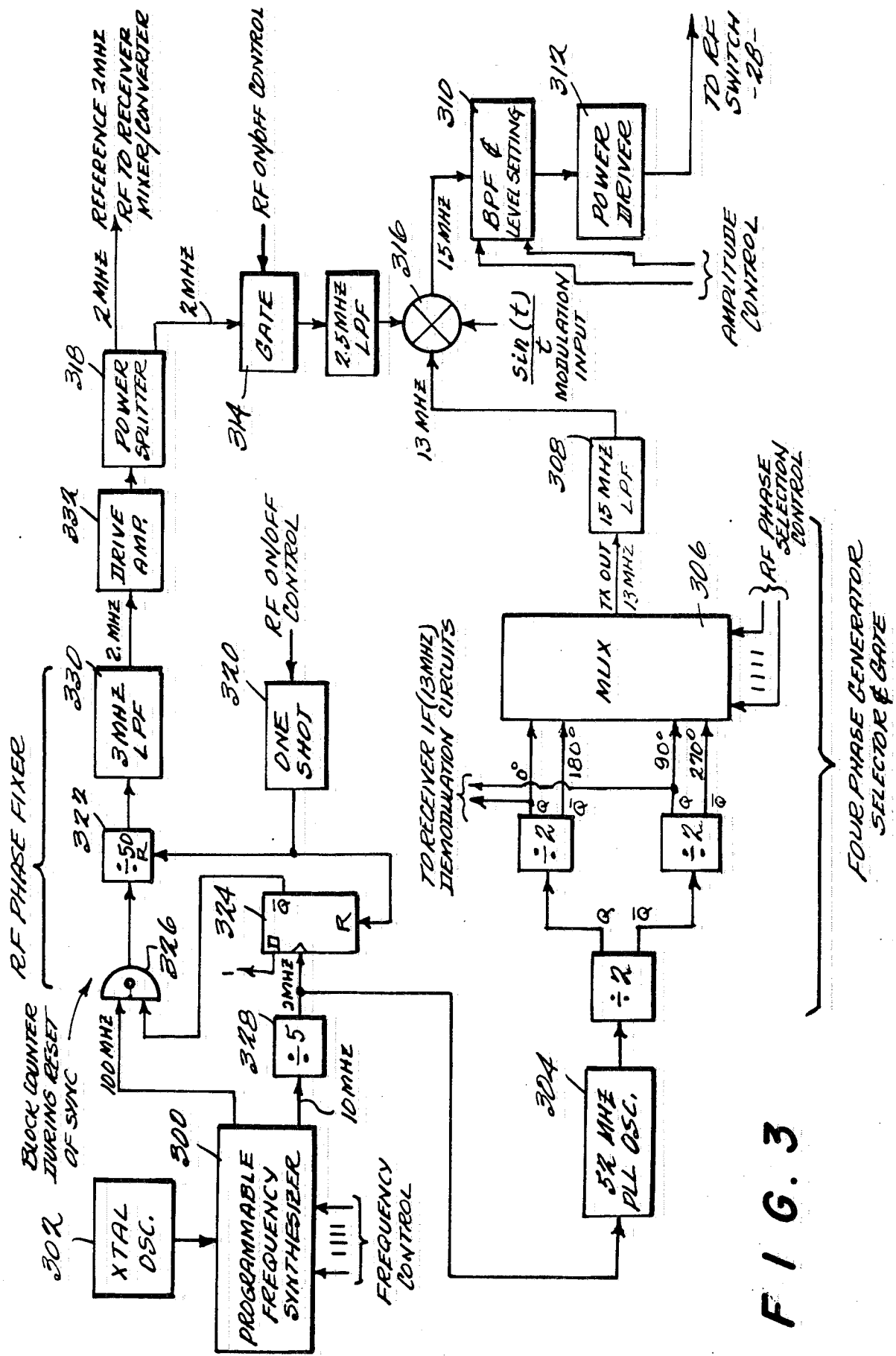
FIG. 3 is more detailed diagram of relevant phase controlled portions of the r.f. transmitter shown in FIG. 2.

The apparatus employed in the presently preferred exemplary embodiment of this invention is substantially the same as that employed and disclosed in our above-referenced copending patent application from which FIGS. 1-3 have been copied. The functional differences in this equipment and in its operation which permit one to practice the presently described and claimed invention are achieved by re-programming the gradient/r.f. pulse sequences used to generate and capture the desired spin echo signal responses and in the manner in which the digital data signal processing computers are programmed to reconstruct a desired array of pixel value signals to be used in generating a visual image of the spatial distribution of nutated nuclear densities throughout a given region of interest in an object under test.

Referring to FIG. 1, the present exemplary embodiment of this invention includes a static field magnetic coil 10 for generating a uniform static magnetic field $H_0$ directed along its axis. The coil 10 is, in the exemplary embodiment, preferably large enough to receive a human body and is preferably surrounded by a cryogenic housing 12 filled with liquid helium or the like so as to permit the coil 10 to be superconducting. In the exemplary embodiment, the static field is of approximately 3.5 KG thus making hydrogen nuclei exhibit NMR at approximately 15 MHz frequency. The X gradient coils, Y gradient coils and Z gradient coils shown in exploded perspective at FIG. 1 are actually concentrically superimposed within the static field magnetic coil 10 and are preferably constructed so as to receive at least a portion of the human body therein. The RF transmit/receive coil (not shown in FIG. 1) is also of conventional design (as are the other coils shown in FIG. 1) and is designed so as to cause the RF magnetic field to be perpendicular to the static magnetic field $H_0$ as will be appreciated by those in the art.

Exemplary electronic apparatus for sequentially driving the various magnetic and RF coils is shown in detail at FIGS. 11A and 11B of our earlier referenced issued patents. For clarity, that apparatus has been shown in simplified form at FIG. 2 of this application and the phase-controlling portion of the RF transmitter circuitry is shown in more detail at FIG. 3.

Referring to FIG. 2, a computerized control system 20 is in communication with the data acquisition and display computer 31 via a serial line link. This control system constitutes the NMR system control which controls the amplitude, timing and/or phasing of the necessary transmitted RF pulses, current drives to the magnetic gradient coils and RF detection processes required for NMR. It includes conventional data storage, data output/input and data entry components as appropriate to the requirements of a particular installation. The computer control system 20 typically also comprises plural data processors operating in parallel under control of a host data acquisition and display processor 31 as will be understood from our earlier referenced copending applications. Except for the particular novel NMR measurement and reconstruction sequences and/or functions to be performed (e.g. as set forth in the illustrative flow diagrams of computer programs), the NMR system control 20 is of conventional design or as described in our earlier referenced copending application and patents. If desired, an array processor (e.g., CSPI Co. Model MAP 200) may be incorporated in the digital signal processing circuits to speed the required reconstruction data digital signal processing.

The RF coil 22 is of conventional design and is used for both transmitting and receiving RF energy to/from the object under test. It is selectively communicated with by either the RF transmitter 24 or the RF receiver and A/D converter 26 via an RF switch 28 which is, in turn, controlled via a control line by the NMR system control 20. This portion of the apparatus is used for selectively transmitting nutation pulses of RF energy into the object under test (said pulses having programmable amplitude, frequency, phase and duration so as to effect a desired nuclei nutation) and for selectively detecting NMR r.f. spin echo responses from the object under test during programmable listening periods. Except for the phase control of the RF signal generator (as depicted in FIG. 3), the RF transmitter 24, RF receiver and A/D converter 26 and RF switch 28 may be of the type described in greater detail in our earlier referenced issued patents.

The magnetic gradient coil drivers 30 are controlled by the NMR system control 20 to selectively drive the X gradient coil, Y gradient coil and Z gradient coil with currents of programmable magnitude, duration, polarity, etcetera all as described in more detail by the earlier referenced U.S. patents.

Because spin echo signals from different measurement cycles are combined in the exemplary embodiment before Fourier transformation or other multi-dimensional reconstruction processes, improved system performance can be obtained under certain conditions (e.g. where there is a residual FID component of error in the spin echo) if the relative phase of the RF excitation signals (and of reference RF signals used for frequency translation and synchronous demodulation in the receiver circuitry) are accurately controlled and phased relative to the initiation of each RF pulse and/or RF detection window. To achieve this precise phase control with respect to the on/off control of RF pulses, the RF transmitter 24 has been modified as shown in FIG. 3.

A programmable frequency synthesizer 300 is conventionally driven by crystal oscillator 302 and by digital frequency control signals from the NMR system control 20 to provide output signals of different frequency as required to address the Larmor frequencies of selected volumes of nuclei as should be apparent. Since the approximate center Larmor frequency involved in the scanning of the exemplary embodiment is 15 MHz, the explanation of the RF signal generating circuitry shown in FIG. 3 will be made at this center frequency. However, it should be understood that the actual frequency of operation will be shifted from this center frequency (both up and down) as necessary to address selected volumes of nuclei in accordance with the teaching of our earlier referenced copending application and patents. For example, the frequencies may be shifted at 1 KHz steps on either side of the 15 MHz center frequency.

At the center frequency operating point, the programmable frequency synthesizer 300 produces synchronous 100 MHz and 10 MHz output signals. The 10 MHz output is divided by 5 to provide a 2 MHz reference signal used to control a 52 MHz phase locked loop oscillator 304. The 52 MHz output is then divided by 4 to provide a 13 MHz IF signal. As shown in FIG. 3, three flip-flops or divide by two circuits are utilized to provide 13 MHz IF signals at 0°, 90°, 180° and 270° relative phase. One of these four available 13 MHz IF signals is then selected by the multiplexer 306 under control of the NMR control computer 20. The 0° and 90° phase 13 MHz IF outputs are provided to the synchronous demodulator circuits of the receiver. The multiplexer selected 13 MHz IF output is then passed through a low pass filter 308 and mixed with a 2 MHz signal to provide a 15 MHz NMR excitation signal. As explained in our earlier referenced copending applications, this excitation RF signal is preferably modulated by a sinc(t) function before passage through a band pass filter and level setting circuitry 310 and on to power drivers 312 and, through the RF switch 28, to drive the RF coil 22.

An RF excitation pulse of the proper width is produced by an RF on/off control signal in conjunction with the gate 314 which only passes the 2 MHz conversion signal to mixer 316 for the desired pulse duration. In addition, suitable amplitude control can be provided to the level setting portion of circuits 310 if desired under control of the computer control system 20.

As shown in FIG. 3, a 2 MHz reference signal is generated and, after power splitting at 318, is provided both to the receiver IF mixer/converter and to the transmitter mixer/converter 316. By carefully controlling (e.g., resetting) the phase of this 2 MHz reference signal, the relative phase of both the transmitted RF signals and of the reference RF signal provided to the receiver mixer/converter can be carefully controlled so as to provide more precisely repeatable NMR pulse echo measurements during successive measurement cycles.

In the exemplary embodiment of FIG. 3, this precise phase control is obtained by an "RF phase fixer" which utilizes a relatively high frequency output from the frequency synthesizer (e.g., 100 MHz) and a resettable frequency divider. In particular, the RF on/off control signals from the NMR system control 20 are presented to a one-shot 320 which preferably triggers on both positive going and negative going transitions. When triggered, one-shot 320 resets counter or frequency divider 322 and flip-flop 324. The $\overline{Q}$ output of flip-flop 324 also blocks gate 326 so as to hold the counter 322 in a fixed state until the next 2 MHz signal transition coming from divider 328. At that precise instant (always in phase synchronism with the 0°, 90° 13 MHz IF reference signals provided to the receiver), gate 326 is permitted to pass the 100 MHz output of the frequency synthesizer 300 which, after division by 50 and passage through a low pass filter 330, provides a 2 MHz output. The 2 MHz output from the low pass filter 330 is then amplified at 322 and passed on to the power splitter 318 to provide the 2 MHz frequency conversion signals previously described.

Accordingly, at the initiation time of each RF excitation pulse, the RF reference and transmitted signals are mutually reset and synchronized with one another. Additionally, since one-shot 320 also triggers at the termination of each RF on/off excitation control pulse, these same RF signals are similarly reset in phase at the termination of each transmitted RF pulse thus ensuring proper frequency conversion and synchronous demodulation in the receiver circuitry in a manner that is more precisely repeatable from one measurement cycle to another. As should be appreciated, a separate one-shot or other circuit could be provided for synchronizing the RF signals in phase at some other predetermined time prior to the detection window of the RF receiver circuitry.

Conventional data entry devices are associated with NMR control computer 20 in FIG. 2 to permit selection of a desired machine parameter value for the TR and/or TE parameters. TR and TE are the American College of Radiology standard symbols for the parameters which we formerly called 6 and 9 parameters. TR is the repetition time of the sequence and affects T1 contrast. TE is the time of the spin echo after the 90° pulse and affects T2 contrast. For example, as shown a select machine parameter input 32 is provided. In the preferred exemplary embodiment, the selection means 32 for selecting the a and b machine parameters is the same keyboard used for other operator interfaces with the NMR system control 20. For example, the keyboard is typically incorporated as part of a conventional video display/keyboard input/output terminal device connected to one of the data processors of the NMR system control through the data acquisition and display computer 31 and associated serial line links as shown in FIG. 2. As will be appreciated, separate dedicated switches could also be provided if desired for this machine parameter selection function. In the exemplary embodiment, the TR and TE parameters are operator selected and are achieved by changing the delay times included in a programmed sequence (shown in detail in FIGS. 6A-6E of our earlier referenced copending application).

Figure 4:
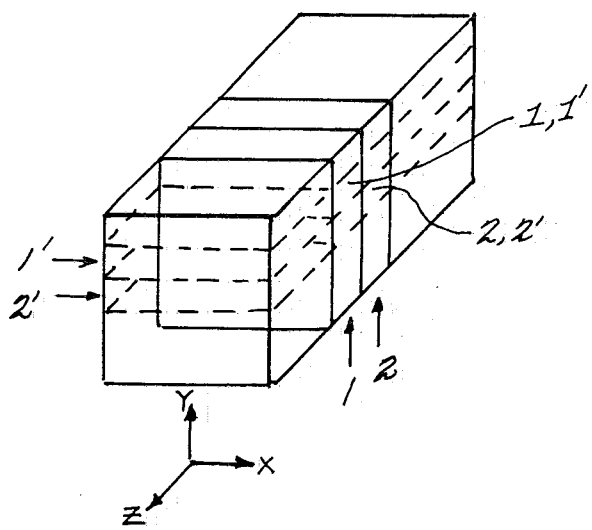
FIG. 4 is a schematic illustration of a line-by-line NMR imaging technique described more fully in our earlier copending application and/or patents and is also a schematic depiction of an embodiment of the present invention wherein a desired sub-volume of an object is selected by the intersection of two generally transverse planar volumes of substantially equal thicknesses.

In the exemplary embodiments of our earlier patents and/or copending application, the rapid multiple plane imaging feature (i.e., time/spatial division multiplexing) was used to advantageously implement a line-by-line imaging technique. For example, as schematically depicted in FIG. 4, the nuclear spins in planar volume 1 were first selectively nutated or flipped by 90°. After a time t, the nuclear spins in planar volume 1' were selectively nutated or flipped by 180°. The nuclear spins within the intersection of regions 1 and 1' will, after another time delay t, produce an NMR spin echo signal.

If the planar volumes 1 and 1' are both relatively thin, then the intersection of them will define a line volume. By subjecting the object to a magnetic gradient along the direction of the line volume during read out of the spin echo signal, it becomes phase encoded such that the amplitude of the frequency components resulting from a Fourier transformation of the spin echo signal represent the relative spin densities at corresponding point volumes along the line volume.

In a line-by-line imaging technique, the successive line volumes of a given planar "slice" through the object are obtained by moving the line volume throughout the desired slice. However, once the nuclear spins in regions 1 and 1' have been disturbed, they must be allowed to return to their equilibrium state for a time delay on the order of the spin-lattice relaxation time T1. The time required to produce and record a spin echo (or spin echoes if more than one 180° nutation pulse is successively applied) is relatively short compared to T1 (a typical spin echo recording cycle may be less than 100 milliseconds while T1 may be on the order of 1,000 milliseconds).

Accordingly, if a line-by-line imaging technique is used to capture NMR response data throughout only a single "slice" of interest, the effective useful duty cycle of the data gathering process will be relatively low. However, as described in our previous patents and/or copending application, a rapid multiple plane imaging technique may be utilized under these circumstances to greatly increase the effective useful duty cycle of the data gathering routine where one is ultimately interested in images from several different "slices" through the object.

For example, any remaining region of the object not affected by previous r.f. nutation pulses (i.e., any past such pulses have been selectively applied to other regions such as 1 and 1' or at least have not been applied within the last T1 time delay period) can be imaged while the earlier imaged volume is relaxing toward equilibrium. Thus, for example, as shown in FIG. 4, a second region 2 may be selectively excited with a 90° nutation pulse and another region 2' selectively excited with a 180° nutation pulse so as to produce NMR spin echo (es) from the intersecting region 2, 2'. As explained in our earlier patents and/or application, one can continue this process in rapid succession so as to rapidly acquire NMR spin echo response signals from a "diagonal" set of intersecting regions during a single T1 time interval. Where the selectively excited subvolumes of the object comprise relatively thin planar volumes, this technique provides a way to image multiple "slices" through the object on a line-by-line basis in a relatively short time period.

However, as earlier mentioned there are theoretical signal-to-noise advantages which can be obtained if the NMR spin echo signal to be measured has emanated from a relatively larger volume of the object to be imaged. Under those circumstances, since considerably more than a single line-volume gives rise to the NMR signal response, multi-dimensional reconstruction processes must be used to extract a point-by-point spatial spin density distribution from the measured NMR response signals.

As also earlier explained, there are prior art techniques that have been proposed to take advantage of such known improved signal-to-noise ratios by obtaining NMR response signals from larger volumes and then using various multi-dimensional reconstruction techniques to extract the required point-by-point density data. However, it is believed that most prior art techniques have employed an NMR signal generation cycle which effectively prevents one from gathering NMR responses from more than a single sub-volume (e.g., a planar volume or "slice") within any given spin-lattice relaxation time period T1. This implies a relatively low effective duty cycle for the data gathering function. This limitation is implied due to the fact that such prior art techniques, in one way or another, tend to disturb the nuclear spins throughout the entire object sometime during a given measurement cycle designed to elicit NMR responses from a selected sub-volume. Thus the entire object must be permitted to relax for a T1 period before more NMR data can be obtained. A few prior art techniques do gather data from a single subvolume by using a single selective 90° pulse and recording an FID or spin echo produced by gradient reversal. They do not avail themselves of the benefits of spin echoes produced using 180° pulses. Others use a non-selective 180° pulse which prevents rapid imaging of other planes.

On the other hand, our sequence of eliciting NMR spin echoes from a desired sub-volume by selectively flipping nuclei by 90° and later by 180° only in selected sub-volumes of the object under test (i.e., all disturbances to nuclear spins are restricted to localized regions), permits one to simultaneously achieve the higher signal-to-noise ratio benefits (which arise from using NMR response signals emanating from larger volumes in conjunction with multi-dimensional reconstruction processes) and our rapid multiple plane imaging techniques which maintain a relatively high effective duty cycle of useful data gathering functions.

Figure 5:
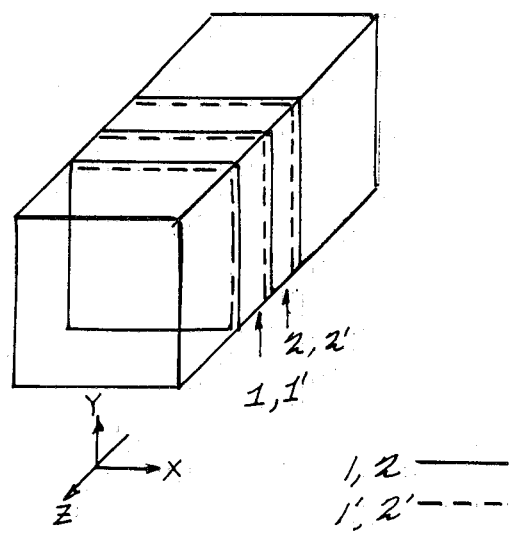
FIG. 5 is a schematic depiction similar to FIG. 4 but illustrating another embodiment of this invention wherein the selected sub-volumes of the object under test are selected by co-planar volumes (or substantially co-planar volumes) successively excited with 90° and 180° nutation pulses.

For example, FIG. 5 illustrates one embodiment where NMR responses are elicited from a planar region or sub-volume such that two-dimensional reconstruction processes must be utilized to extract the desired point-by-point density distribution within the plane. Thus, a planar volume 1 is selectively irradiated by a 90° r.f. nutation pulse and, subsequently, a substantially coplanar sub-volume or region 1' is irradiated by a 180° r.f. nutation pulse. Since their intersection is, in this instance, also substantially the same planar volume, it follows that the subsequent NMR spin echo signal response will emanate from the entire selectively irradiated planar volume. Thus, line density distributions and/or point density distributions within the plane must be deduced by one or two-dimensional reconstruction processes respectively.

However, since the selective irradiation processes utilized to elicit NMR spin echo response from planar volumes 1, 1' have not disturbed the nucler spins elsewhere within the object, our rapid multiple plane imaging feature still may be simultaneously realized. For example, after NMR spin echo response data from planes 1, 1' have been acquired, planar volume 2 may be immediately selected and irradiated by another 90° r.f. nutation pulse. After an appropriate short time delay, a coplanar volume 2' will be selectively irradiated by a 180° r.f. nutation pulse so as to generate NMR spin echo response signals from planar volume 2, 2' while planar volume 1, 1' is still returning toward equilibrium during its T1 spin-lattice relaxation time. A number of successive planar volumes can be processed in this way during a single T1 recovery time. For example, if the data acquisition time for a given planar volume is on the order of 100 milliseconds and the T1 recovery time is on the order of 1,000 milliseconds, ten planar volumes can be processed in rapid succession so as to acquire image-producing data therefrom in the same time that would otherwise be required to obtain the necessary image data from only a single plane having the same T1 recovery time.

Furthermore, since the 90° and 180° nutation pulses select a common volume, there is no expected interference due to a residual FID from volumes selected by the 90° nutation pulse but not by the 180° nutation pulse. Accordingly, this effectively eliminates the desire or need for applying a particular sequence of differently phased r.f. nutation pulses with particular combinations of the resulting spin echo signals as in a line-by-line imaging process of the type described in our earlier referenced copending application. Of course, this particular sequence of phased nutation pulses and combination of spin echo signals would still have an advantage if the 90° and 180° nutation pulses do not select exactly the same planar volume.

Figure 6:
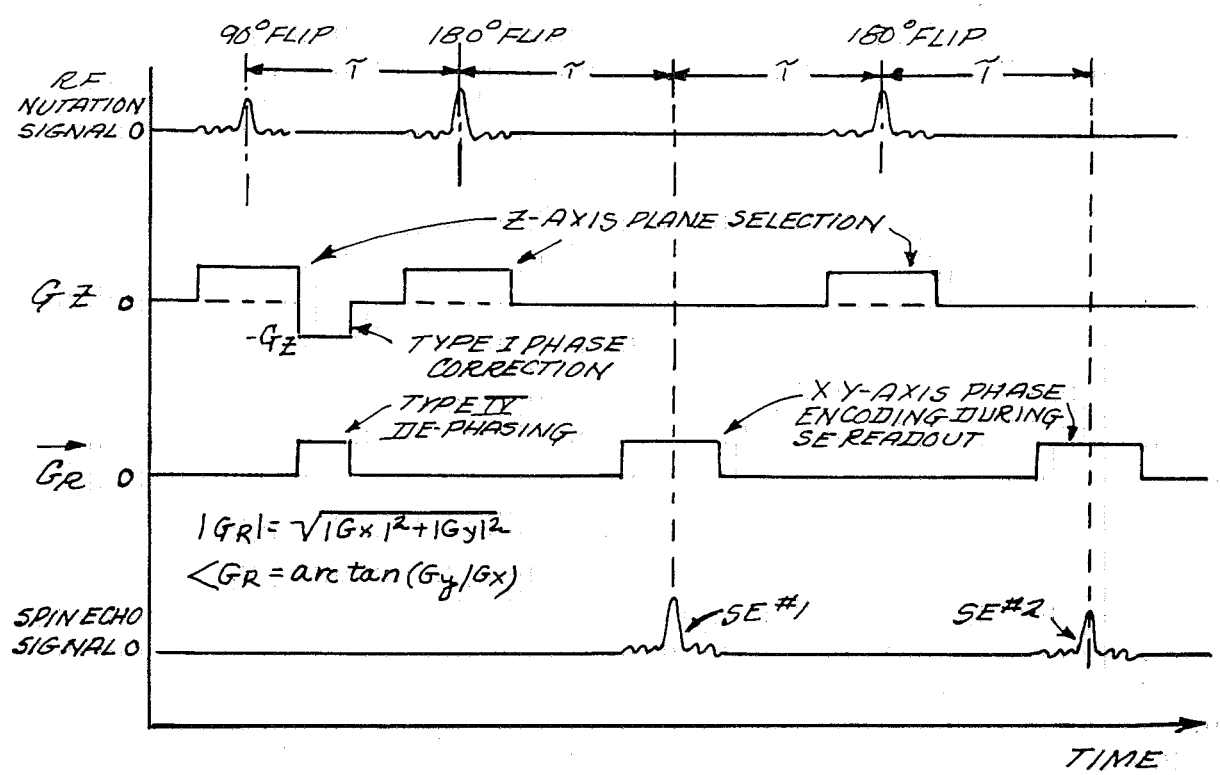
FIG. 6 is a graph of exemplary gradient/r f. pulse sequences for an exemplary planar imaging embodiment of this invention achieving reconstruction from one-dimensional projections taken at successive different angular orientations.

A typical elementary sequence of magnetic gradients and r.f. nutation pulses used for such planar volume imaging (and using a reconstruction process which employs multiple angle projections) is shown at FIG. 6. The 90° and 180° r.f. nutation pulses are sinc function modulated as before so as to provide a precisely defined "rectangular" frequency spectrum with their center frequencies being controlled so as to correspond to a selected planar volume within the object at various spacings one from the other. The three-dimensional coordinate system that has been assumed for purposes of explanation is reiterated in FIGS. 1, 4 and 5 where Z is assumed to be along the axis of the patient, X is assumed to be from the patient's left-to-right side and the Y axis is assumed to lie along the patient's front-to-back dimension. It should be understood other coordinate conventions could just as well have been assumed.

The Z axis magnetic gradient $G_z$ is depicted in FIG. 6 as being "on" during each of the r.f. nutation pulses so as to selectively irradiate the same planar volume in each instance of a given measurement cycle. As should be appreciated, only a single elementary measurement cycle for a single planar volume is depicted in FIG. 6 but other subsequent measurement cycles would be similar except that the frequency of the nutation pulses (and/or the strength of the $G_z$ gradient) would be changed so as to select a different planar volume. For additional projection angle orientations this cycle would be repeated with the radial magnetic gradient $G_r$ changed in angular orientation.

The $G_z$ gradient is reversed for a short time following the 90° nutation pulse so as to re-phase the spins with a type I phasing correction as described in our earlier patents and/or copending application. The radial magnetic gradient $G_r$ is realized by various combinations of the X axis and Y axis magnetic gradients Gx and Gy, respectively, so as to determine the resultant angle of a resultant radially directed magnetic gradient in accordance with the usual trigonometric rules as depicted in FIG. 6.

The gradient $G_r$ is switched "on" somewhere between the 90° nutation pulse and the first 180° nutation pulse, (preferably closer to the 90° nutation pulse) so as to purposefully cause the nuclear spins to de-phase in this dimension. This is a type IV de-phasing pulse as described in our earlier patents and/or copending application.

Subsequently, after the spins in the selected volume are all inverted by a 180° nutation pulse, the radial gradient $G_r$ is again switched "on" so as to purposefully re-phase the nuclear spins in the radial dimension and thus produce the first spin echo signal as depicted in FIG. 6. The application of magnetic gradient $G_r$ during the spin echo signal not only acts to re-phase the nuclear spins in this dimension (and thus to help produce the spin echo) and thereafter to controllably de-phase again in anticipation of a following spin echo generation cycle, but also so as to phase-encode the spin echo signal such that each point (i.e., the amplitude of each frequency component) in its Fourier transform represents a projection of the spin densities through the object as projected onto a line perpendicular to the axis of the radial gradient (e.g., at the angle of $G_r$).

In this way, a one-dimensional projection of the point-by-point spin densities throughout the plane is obtained at a given angular orientation. For each planar volume, this measurement sequence is repeated for each desired angle so as to permit averaging or other accumulation of similar spin echo signals. (As should be appreciated, separate respective signal accumulations or averaging processes are employed for each of the first and second and any subsequent spin echo signals generated in a given measurement cycle.) Similar (averaged) spin echo signals are obtained for each desired projection angle to be used in a conventional multiple angle projection reconstruction process (e.g., typically convolution and back-projection processes of the type used for computed X-ray tomography).

The elementary sequence of a single measurement cycle for a single planar volume as depicted in FIG. 6 may be immediately repeated for the next adjacent or other planar volume for which an image is desired while the first or other earlier excited planar volumes are still relaxing toward equilibrium during their respective T1 time delay periods. Of course, center frequencies of the 90° and 180° r.f. nutation pulses would be appropriately changed in each cycle so as to select the desired next plane during subsequent repetitions of the basic measurement cycle depicted in FIG. 6.

Processes for reconstructing a point-by-point two-dimensional distribution of values from a plurality of one-dimensional projections taken at multiple relative angular orientations are well known in the art. For example, see Lauterbur, P.C., "Image Formation by Induced Local Interactions: Examples Employing Nuclear Magnetic Resonance", *Nature* (London) 242:190, 1973 and/or Bottomley, P.A., "NMR Imaging Techniques and Applications: A Review.", Review of Scientific Instrumentation, 53(9), 1319–1337 (1982). A brief outline of typical such techniques is now presented:

Let $S_n(t)$ = accumulated (averaged) spin echo signals for each different angular orientation of the radial gradient $G_{rn}$(n=1, 2, 3, . . . n).

Then the Fourier transformed (averaged) spin echo signal $$F(S_n) = S'_{n1} + S'_{n2} + S'_{n3} + \ldots S'_{nm} \qquad \text{(Equation 2)}$$

where $S'_{nm}$ = the sinusoidal signal component at frequency $f_m$, the amplitude of which, in turn, represents the magnitude of a projected column of spin densities at a corresponding spatial location along a line perpendicular to the particular angular orientation of $G_{rn}$ then existing. Thus each such Fourier transformed (averaged) spin echo signal represents a sampled version of a one-dimensional projection of the spin densities within the selected planar volume at the angular orientation of $G_{rn}$.

Thus an array of such sampled one-dimensional spin density projections is formed with each line in the array representing such a projection at a particular angular orientation:

$$\text{angle } 1 = S'_{11}, S'_{12}, S'_{13}, \ldots S'_{1m} \quad \text{(Equation 3)}$$
$$\text{angle } 2 = S'_{21}, S'_{22}, S'_{23}, \ldots S'_{2m} \quad \text{(Equation 4)}$$
$$\text{angle } 3 = S'_{31}, S'_{32}, S'_{33}, \ldots S'_{3m} \quad \text{(Equation 5)}$$
$$\vdots$$
$$\text{angle } n = S'_{n1}, S'_{n2}, S'_{n3}, \ldots S'_{nm} \quad \text{(Equation 6)}$$

But this merely presents the now well known (and solved) problem of reconstructing a two-dimensional image from a multiplicity of its one-dimensional projections taken at different angular orientations. The solution may be any one of the multiple angle projection reconstruction processes now well known and used, for example, in X-ray computed tomography and electron microscopy. One popular and usable form of solution is the so-called filtered back-projection or convolution/back-projection reconstruction processes which need not be described here in detail.

An illustrative simplified segment of a suitable computer program to be used in the apparatus of FIGS. 1–3 so as to realize the two-dimensional multiple angle projection reconstruction technique of FIG. 6 (and 10) is depicted in flow chart form at FIGS. 18A–18B. For example, at box 1800, suitable initialization procedures are followed such as, for example setting counters m and n to zero and q to one. Thereafter, the n counter is incremented at box 1802 and the Z-axis magnetic gradient is set to the desired value at 1804 in preparation for the transmission of an appropriate 90° r.f. flip pulse for a desired planar volume $P_n$ as denoted in box 1806 at FIG. 18.

After the 90° nutation pulse terminates, an appropriate $-G_z$ re-phasing gradient is generated at 1808 as is a controlled de-phasing radial gradient field $G_{rq}$ where q represents the particular angular orientation of $G_r$ for the measurement cycle. $-G_z$ and $G_{rq}$ are then turned off at 1809. Thereafter, the Z-axis $G_z$ is set once again at 1810 in preparation for the transmission of the first 180° r.f. flipping pulse for plane $P_n$ as represented at box 1812. Thereafter, at 1814, the Z-axis gradient is turned off and the radial gradient $G_{rq}$ is turned on and remains on throughout the duration of read out process depicted at 1816 where the first spin echo signal is read, stored and accumulated within the earlier similar spin echo signal for this particular plane and this particular angular orientation.

At 1818, the radial gradient is turned off while the Z-axis gradient is turned back on again in preparation for the transmission of the second 180° r.f. flipping pulse at 1820. Thereafter, the Z-axis gradient is once again turned off at 1822 and the radial gradient is turned back on again in preparation for the read out processes of box 1824 where the second spin echo signal is read out, stored and/or accumulated with similar spin echo signals for that particular plane and angular orientation. Thereafter, this particular measurement and data gathering subcycle terminates by turning off the radial gradient at 1826.

A test is made at 1828 to see if all of the ten planes to be rapidly measured in the rapid plane imaging feature have been serviced. If not, control is returned to box 1802 where the n counter is incremented and another elemental data taking subcycle is repeated.

Eventually, all ten successive planes will have been serviced and the program will progress to box 1830 where the m counter is incremented. In this illustrative example, m is used to keep track of the number of times similar first and second spin echo signals have been measured for a particular plane at a particular angular orientation. This counter may also be used to determine the desired relative phases of the 90° and 180° nutation pulses and whether the newly-acquired spin echo signal is to be added or subtracted from the accumulated (averaged) signal on any given pass through the elemental measurement subcycle just described. In the illustrative example, the maximum value of the m counter is 4 which represents the minimum number of similar spin echo signals that must be measured and accumulated if it is necessary or desirable to eliminate the residual FID signal component as should now be understood in view of the earlier discussion.

If the maximum m counter contents have not yet been reached as tested for at 1832, then the n counter is reset to zero at 1834 and control is again returned to box 1802 for another ten repetitions of the elemental measurement sub-cycle. On the other hand, if the maximum m counter content has been reached, then control is passed to 1836 where the n and m counters are reset to zero. As earlier explained, the q counter determines the particular angular orientation of the radial magetic gradient. If the desired maximum q counter content has not yet been reached as tested at 1838 (typically at least 180° and possibly 360° are typically covered at small increments of one degree or less in angular orientation between successive projections), the q counter is incremented at 1839 and control is again returned to box 1802 for additional repetitions of the measurement subcycle at progressive angular orientations.

Once the required number of multiple angular one-dimensional projects have been taken, then the accumulated first and second spin echo signals are Fourier transformed at 1840 for each angular orientation so as to obtain the required one-dimensional projections of spin densities at each corresponding angle for each plane $P_n$. Thereafter, conventional reconstruction processes (e.g., convolution/back projection) are employed at 1842 to reconstruct display pixel values over each plane $P_n$ to be used in driving a subsequent visual display. The pixel values for a desired plane $P_n$ are selected and displayed in conventional fashion (e.g., in the same way as this is done in computed X-ray tomography apparatus) at 1844.

A typical exemplary sequence of magnetic gradients and r.f. nutation pulses for planar imaging using a two-dimensional Fourier transformation process is depicted at FIG. 7. Two-dimensional Fourier transform techniques for planar imaging of NMR signal responses was earlier proposed by Kumar et al, "NMR Fourier Zeugmatography", Journal of Magnetic Resonance, 18:69 (1975) and has later been improved and referred to as "spin warp imaging" by Edelstein et al in "Spin Warp NMR Imaging and Applications to Human Whole-Body Imaging", Physics in Medicine and Biology, 25 (4) 751–756 (1980) and a related Hutchison et al International PCT Patent Application No. PCT/GB81/00044, dated Mar. 14, 1980.

The basic pulse sequence of gradient/nutation pulses depicted in FIG. 7 is similar to that already discussed for FIG. 6 except that separate $G_x$ and $G_y$ magnetic gradient components are now shown because a rectangular coordinate system is employed. For any given measurement cycle, the Y axis gradient $G_y$ encodes a phase dependence in the subsequent spin echo signal(s) as a function of vertical position (i.e., along the Y axis) in the signal frequency components. The spin echo response is read out with only the X axis gradient $G_x$ switched "on" so that the phase encoded vertical columns of spin density are each projected onto corresponding points in the frequency spectrum of the spin echo signal. The size of the Y axis gradient $G_y$ occurring between the 90° and first 180° nutation pulse is changed for each desired level of vertical spatial encoding as indicated in FIG. 7 by dotted lines. In general, in the preferred embodiment, the number of projections collected along the Y axis equals the number of desired pixel values to be displayed along the Y axis (i.e., the number of projected vertical columns of spin densities earlier discussed, usually, in the exemplary embodiment, 128 or 256). The $G_z$ gradient and $G_x$ gradients are analogous to the $G_z$ and $G_r$ gradients already discussed in the multiple angle projection/reconstruction embodiment of FIG. 6.

The Fourier transformation of a waveform can be accomplished in accordance with well known signal processing functions. In the preferred exemplary embodiment, the well known "Fast Fourier Transform" (FFT) is employed in a digital signal processing implementation of a type generally well known per se in the prior art. To briefly review one two dimensional Fourier transformation process contemplated for this exemplary embodiment, the following analysis is given:

Let: $S_n(t)$ = accumulated (i.e. averaged) spin echo signals for each different Y-axis gradient $G_{yn}$ (n = 1, 2, ... n) then the Fourier transformed (averaged) spin echo signal $$F(S_n) = S'_{n1} + S'_{n2} + S'_{n3} + \ldots S'_{nm} \qquad \text{(Equation 7)}$$

where $S'_{nm}$ = the sinusoidal signal component at frequency $f_m$, the amplitude of which, in turn, represents the magnitude of a projected vertical column of spin densities with phase encoding $G_{yn}$ corresponding to a particular vertical level within that column at a location along the X-axis represented by $f_m$ (due to the X-axis phase-encoding during readout of the spin echo signal).

Thus an array of such one-dimensional spin density projections is formed, with each line in the array having different vertical level (Y-axis) phase encoding:

| | |
|---|---|
| level 1: $S'_{11}, S'_{12}, S'_{13}, \ldots S'_{1m}$ | (Equation 8) |
| level 2: $S'_{21}, S'_{22}, S'_{23}, \ldots S'_{2m}$ | (Equation 9) |
| level 3: $S'_{31}, S'_{32}, S'_{33}, \ldots S'_{3m}$ | (Equation 10) |
| . | |
| . | |
| level 4: $S'_{n1}, S'_{n2}, S'_{n3}, \ldots S'_{nm}$ | (Equation 11) |

Now it may be observed that the values of the array members in any vertical column can be treated like samples of a vertical line-volume spin echo read out with Y-axis phase encoding therealong. Thus, by performing a second dimension of Fourier transformation on this derived sampled waveform (i.e. along each vertical array column), pixel values representing nutated nuclear density may be derived for each point volume in the planar volume from which the spin echo signals came. That is, if the derived phase-encoded waveforms in the vertical dimension are denoted by $Q_m$ where m is the array column number, then $Q_m$ is represented by the sample values:

$$Q_m = S'_{1m}, S'_{2m}, S'_{3m}, \ldots S'_{nm} \qquad \text{(Equation 12)}$$

and $$F(Q_m) = Q'_{m1} + Q'_{m2} + Q'_{m3} + \ldots Q'_{mq} \qquad \text{(Equation 13)}$$

where $Q'_{mq}$ = the sinusoidal signal component at frequency $f_q$, the amplitude of which, in turn, represents the magnitude of spin density in a local point volume spatially located within the planar volume at an X-axis position corresponding to $f_m$ and a Y-axis position corresponding to $f_q$.

The result is an array of digital pixel data signals, each representing the spatial spin density at a corresponding elemental "point" volume within the selected planar volume. These can be stored and used conventionally to drive a video image display on a CRT. For example, such an array of pixel data signals is depicted below using the above nomenclature where pixel values are depicted for X-axis pixel positions in and Y-axis pixel position q

| | |
|---|---|
| $Q'_{11}, Q'_{12}, \ldots Q'_{1m}$ | (Equation 14) |
| $Q'_{21}, Q'_{22}, \ldots Q'_{2m}$ | (Equation 15) |
| $Q'_{31}, Q'_{32}, \ldots Q'_{3m}$ | (Equation 16) |
| . | |
| . | |
| $Q'_{q1}, Q'_{q2}, \ldots Q'_{qm}$ | (Equation 17) |

Where the subscript m corresponds to frequencies $f_m$ representing X-axis pixel locations and the subscript q corresponds to frequencies $f_q$ representing Y-axis pixel locations as explained above.

The flow chart shown in FIGS. 19A and 19B is similar to that shown in FIGS. 18A and 18B except that it is intended to illustrate the implementation of a two-dimensional Fourier transform reconstruction technique for the embodiment of FIG. 7 (and 11). (The three-dimensional Fourier transform embodiment of FIG. 16 would be directly similar but would involve an extra Fourier transform step so as to resolve three dimensions into a series of two-dimensional functions which can thereafter be twice more Fourier transformed to resolve the two dimensions into one and then into a point-by-point nuclear spin density distribution.)

After initializing the counters n, m and q at 1900, the elemental measurement sub-cycle comprising steps 1902 through 1928 is essentially similar to that comprising steps 1802 through 1828 in FIGS. 18A and 18B. The basic difference is that the phase encoding is now done by the Y-axis gradient $G_y$ (in accordance with the contents of counter q) so that the accumulated data is all taken at the same relative angular orientation but is phase encoded for different vertical positions along the Y-axis as should be apparent. The m, n and q counter control functions at steps 1930 through 1939 for controlled repetition of the elemental measurement sub-cycle are exactly similar to the already described steps 1830 through 1839 in FIGS. 18A and 18B.

Once the accumulated (averaged) first and second spin echo signals are thus made available, a first Fourier transform step is performed at 1940 for each encoded Y-axis level so as to obtain spectral points representing phase encoded vertical column functions for each plane.

Thereafter, another dimension of Fourier transformation occurs at step 1942 so as to resolve the vertical column functions into point-by-point pixel values along each column for each plane of interest. Once the array of image pixel values is thus reconstructed, a conventional selection and display of those pixels for any desired plane may be undertaken at step 1944.

It should be understood that the illustrative simplified flow charts of FIGS. 18 and 19 are just that and that many different specific detailed implementations of these desired control functions can be achieved in either computer program software and/or dedicated hardware and/or in mixtures of the same. It will also be understood that within the data processing constraints of any given configuration of digital data processing system used in implementing this invention, it may be desirable to perform at least some of the Fourier transformations or other digital signal processing in a separate array processor or the like as soon as the required input data becomes available in the data capturing process. For such purposes, it may be desirable to incorporate conventional array processors such as the array processor presently commercially available from CSPI Company under Model No. MAP 200.

While the two-dimensional Fourier transform reconstruction technique discussed above in conjunction with FIG. 7 does have some similarities to the prior art "spin warp" imaging, there are also several improvements and differences. For example:

1. The selective nutation of nuclei within only selected subvolumes of the object (e.g. a planar volume) to generate a given NMR signal response (e.g. spin echoes), makes it possible to perform rapid multiple plane imaging processes by time/spatial division multiplexing during a single spin-lattice relaxation time delay T1. (It is possible that the "spin warp" technique could be modified so as to permit similar rapid multiple plane imaging by using different center frequencies for 90° nutation pulses so as to selectively excite only different respective planes. However, one of the measurements of the presently known "spin warp" techniques process the entire sample with 180° nutation pulses so as to invert all spins therewithin during an adiabatic fast passage of a frequency swept pulse which necessarily disturbs the nuclear spins throughout the entire object thus requiring a waiting period of about T1 between useful data gathering processes.
2. The presently known "spin warp imaging" techniques obtain spin echo signals by reversing the $G_x$ gradient to cause dephasing and then rephasing of the nuclear spins. On the other hand, the above proposed technique of FIG. 7 utilizes a 180° nutation pulse affecting only the plane of interest so as to rephase the spins and produce a spin echo. As a result, any inherent dephasing of the nuclear spins caused by inhomogeneity in the magnetic fields is automatically eliminated because the 180° nutation pulse causes this type of dephasing error to be cancelled insofar as the spin echo response is concerned.
3. The use of 180° r.f. nutation pulses to cause the spin echo occurrence also permits the use of additional 180° nutation pulses to produce additional spin echo responses, each of which can be used to produce its own corresponding image (typically after being averaged with other similar spin echo responses). Using at least two such successive spin echo images, one can calculate a T2-parameter NMR image. The prior known "spin warp imaging" processes may also obtain successive spin echoes by continuing to alternate the $G_x$ gradient. However, any distortion in the spin echo due to magnetic field inhomogeneity will become progressively worse in such prior spin warp processes because such errors do not inherently cancel as in the presently proposed process.

If the embodiment of FIG. 7 is used to obtain successive spin echo signals, it should be noted that since each 180° nutation pulse reverses the relative phase of the spin echo signals, the phase encoding due to the Y-axis gradient $G_y$ will be reversed in every successive spin echo signal. As a result, images calculated from successive spin echo signals will be reconstructed upside down with respect to one another. Accordingly, in the preferred exemplary embodiment, the image display computer (or some other signal processing device in the system) is preferably programmed so as to vertically invert the resultant image that is to be displayed.

As earlier explained, there are expected signal to noise ratio advantages obtained when the NMR signal response is elicited from a larger population of nuclei (e.g. as in a planar volume as opposed to a line volume). For example, NMR imaging using signals generated from a planar volume has a signal to noise ratio approximately equal to the square root of the number of different projections used in the reconstruction process over a line-by-line NMR imaging process where the NMR signals are derived from single line volumes at any given time.

Similar signal to noise ratio improvements can be expected for other configurations of subvolumes used in conjunction with multi-dimensional reconstruction processes. For example, referring again to FIG. 4, it will be recalled that a spin echo can be obtained from a limited subvolume 1, 1 . If the planar volume regions 1, 1' are selected to be relatively thin, this will correspond to a limited line volume. However, it is also possible to reduce the selectivity associated with the 90° and/or 180° nutation pulse (i.e., make one or both of the planar volumes 1, 1' relatively thicker) so as to make the subvolume region 1, 1' occupy greater volume and therefore provide inherent signal to noise ratio advantages. For example, if the planar region 1' is made relatively wide, then the selected region 1, 1' will be relatively taller such that it covers a number of line volumes simultaneously. A two dimensional reconstruction process as described above for imaging the entire plane can then be employed to resolve the point-by-point spatial nuclear density distribution throughout the selected subplanar volume.

In addition to the anticipated signal to noise ratio advantages, it will be noted that this selection of a sub-region out of the plane permits one to collect a more limited amount of data that can therefore be more rapidly processed and reconstructed to an image. For example, it may be desirable to collect a relatively small amount of data and reconstruct an image from a large region initially so that a physician may obtain a coarse first image to assist in locating a suspected organ within the NMR imaging apparatus. Then by subsequently concentrating on this desired region, one may obtain a more finely resolved image of the subvolume. If only a relatively smaller subvolume is of interest, then the full resolution capabilities of the apparatus can be concentrated on this relatively smaller region thus permitting a higher resolution image for the smaller region of interest than would otherwise be possible if one were forced by sampling requirements (e.g. because the NMR signals generated by other techniques might have emanated from a larger region) to reconstruct the full extension of the object cross-section with the many more pixels thus being required to obtain the same desired high resolution image. As an alternative or in addition to improving resolution in the subvolume one can concentrate additional averages in the limited region to improve signal to noise in proportion to the square root of the increased time spent gathering the extra averages.

If the sub-planar volume is selected as essentially a "tall" line selected similarly to the line-by-line imaging processes, there are significant subvolume elements that have been excited with the 90° nutation pulse but not the 180° nutation pulse such that interfering residual FID signal components can be expected. Accordingly, as earlier described in our above referenced patents and/or copending application, it is preferable that four different phase variations of the 90° and 180° nutation pulses be used in conjunction with a synchronous detection and averaging of spin echo signals from successive measurement cycles so as to eliminate these interfering FID signal components. As should be understood, this will limit one to the necessity of making at least four or more signal measurement cycles for each projection. The next "tall" line region volume that might be used in the rapid multiple plane imaging process (e.g. time/spatial division multiplexing feature) is a nonoverlapping region such as region 2, 2' shown in FIG. 4. However, since this non-overlapping region is located below and behind the suspected region of interest, there may be nothing of real interest located there or in other possible regions that could be included in rapid multiple plane imaging processes so that one may effectively lose this otherwise advantageous feature for the subplanar region of interest implementation.

At the same time, there are considerable compensations that may be available under these same circumstances in other situations. For example, one may be able to effectively reduce motion artifact in the reconstructed image for some locations of the subvolume region of interest. For example, consider FIG. 8 where a patient (the cylindrical object) has a suspected tumor in the lung which is at the same chest level as the beating heart. A straightforward full planar volume reconstruction process may be degraded due to the motion artifact induced by the heart. However, if a sub-planar region of interest is selected which includes the tumor but not the beating heart, motion artifacts might be eliminated. As depicted in FIG. 8, region 1 is selectively irradiated by the 90° nutation pulse and contains both the beating heart and the suspected lung tumor while region 1' is selectively irradiated with the 180° nutation pulse but contains only the tumor. The resultant NMR spin echo signal thus includes signal components from the tumor but not from the heart.

Since motion artifacts are thus avoided in the spin echo signal per se, it might be assumed that motion artifacts have altogether been avoided under the circumstances of FIG. 8. Unfortunately, that is not so because the heart is located in region 1 and can thus still produce an interfering residual FID signal component. While the 4-phase signal irradiation/ averaging technique described above is designed to eliminate the residual FID components, it is based on the assumption that the residual FID component will be consistent from one measurement cycle to the next. Since the moving heart (or any other relatively moving element) can produce a varying residual FID, it may not be eliminated by the earlier proposed 4-phase signal averaging technique. Thus, the FID component can still produce motion artifact in the image under the situation depicted at FIG. 8.

Although it is not yet known whether this type of potential motion artifact is more or less disturbing than motion artifact in a straightforward component planar-volume reconstruction, even this potential problem can be eliminated if alternative orientations of regions 1 and 1' can be found (as depicted in FIGS. 9 and 9a) which do not include the relatively moving elements. For example, as depicted at FIGS. 9 and 9a, regions 1 and 1' still intersect at the suspected tumor location but they both avoid the beating heart location so it cannot possibly produce even potential residual FID interference with the desired NMR spin echo signal response. The desired re-orientation of the $G_x$ and $G_y$ gradients to rotate the xy coordinates can be obtained by using combinations of $G_x$ and $G_y$ gradients simultaneously to produce a desired resultant in accordance with the usual trigonometric rules.

Figure 10:
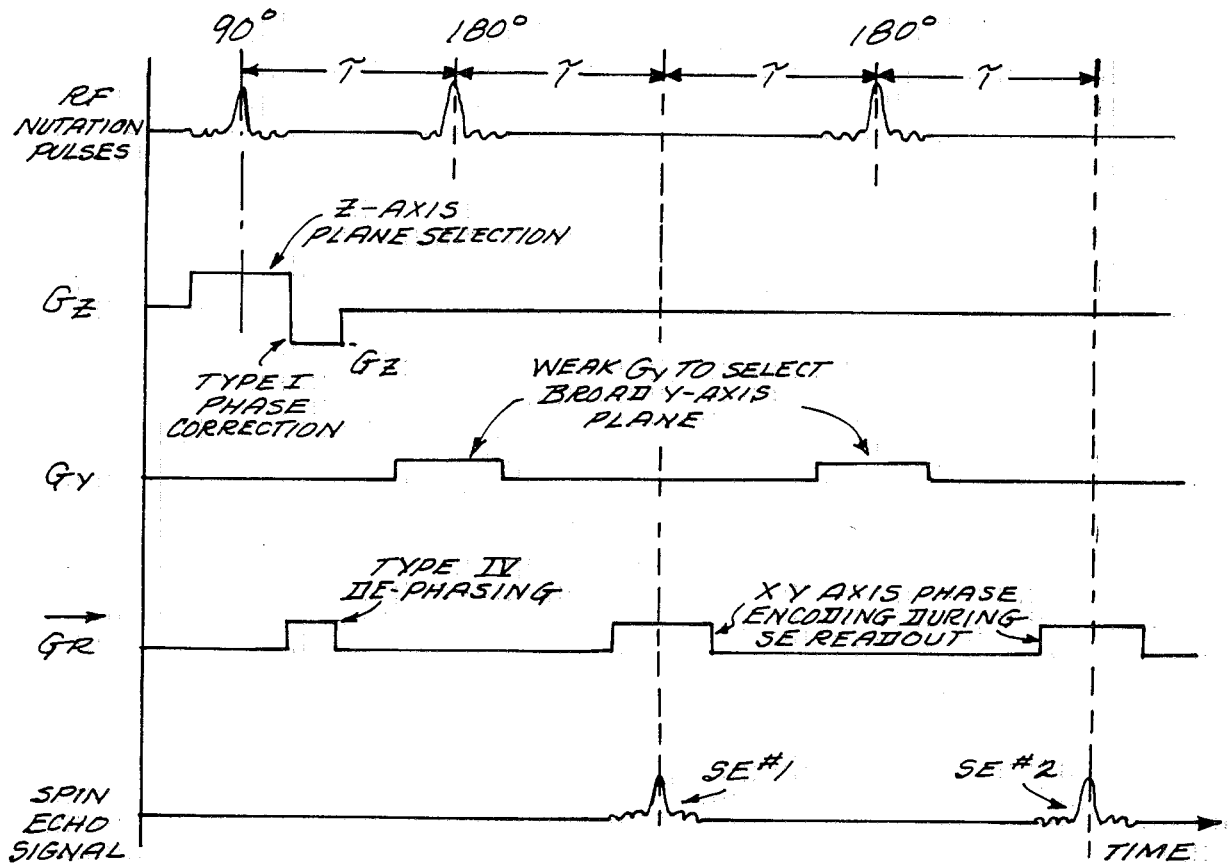
FIG. 10 is an exemplary gradient/r.f. pulse sequence similar to that shown in FIG. 6 but illustrating the selection of a sub-planar region of interest for the multiple angle reconstruction process.

Typical exemplary magnetic gradient and r.f. nutation pulse sequences are shown for sub-planar region of interest imaging at FIGS. 10 and 11 respectively for multiple angle reconstructions (similar in all respects to the FIG. 6 embodiment) and in FIG. 10 for the two dimensional Fourier transform embodiment (similar in all respects to FIG. 7). In these exemplary FIG. 10 and FIG. 11 embodiments, a planar volume is selected by the 90° r.f. nutation pulse and the Z axis gradient $G_z$ just as before. Now, however, the 180° r.f. nutation pulses selectively excite a considerably wider planar region which extends in the vertical Y axis dimension due to a relatively weak Y axis magnetic gradient $G_y$ and/or to a broader frequency spectrum in the 180° nutation pulse. In this way, a sub-planar "tall line" region of interest is selectively excited to produce the spin echo signals.

As before, $G_r$ is a radially directed magnetic gradient used to generate one dimensional projections at various relative angles about the subvolume to be reconstructd. The FIG. 11 two dimensional Fourier transform embodiment uses analogous selection techniques for obtaining a spin echo from the desired "tall line" sub-volume region except that now the radial magnetic gradient $G_r$ is replaced by an X axis gradient $G_x$ and vertical or Y axis information is phase-encoded by stepping the Y axis magnetic gradient $G_y$ to different values on different measurement cycles (as indicated by dotted lines).

Figure 12:
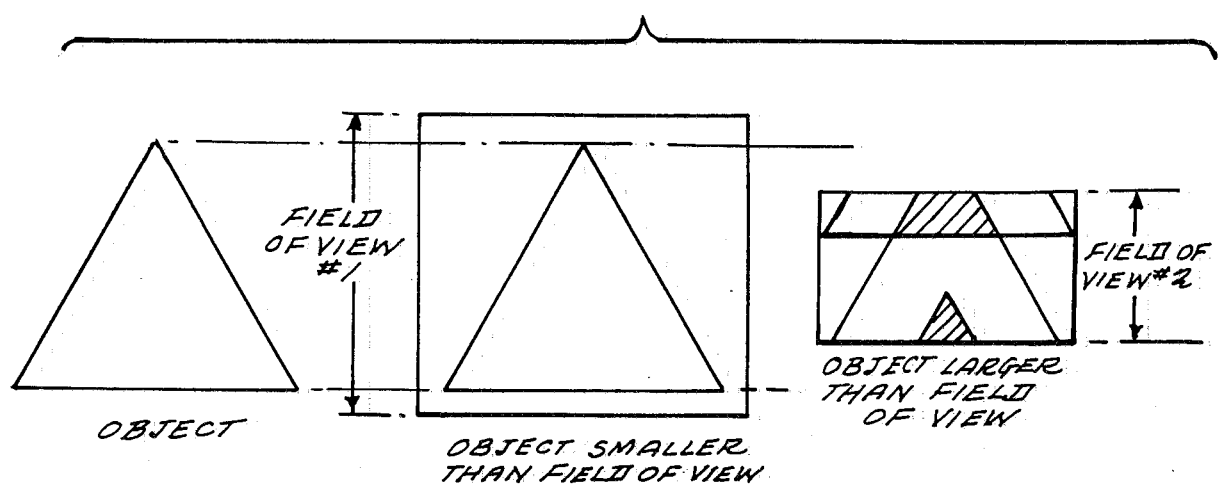
FIG. 12 illustrates the expected aliasing problem to be encountered when the area providing NMR responses in the object under test is larger than the reconstructed field of view.

One possible side effect of using the two dimensional Fourier transform embodiment is that aliasing in the vertical Y axis dimension is produced if the spin echo producing region is larger than the reconstructed field of view. FIG. 12 illustrates the problem. Here, an object to be reconstructed is properly reconstructed and displayed when the field of view is larger (or at least as large as) the object cross-section. However, as also depicted at the extreme right in FIG. 12, if the vertical field of view is smaller than the vertical extent of the object to be reconstructed, then the top and bottom of the object will "wrap around" on top of each other due to the aliasing problem.

To avoid this type of aliasing problem, one should therefore ensure that the region of interest used to produce spin echo signals is no larger than the reconstructed field of view. A more subtle related problem is that the same type of aliasing problem can nevertheless still be encountered if the region of interest generating-spin echo signals is not centered vertically within the Y axis gradient field. If not so centered, then the reconstructed image will alias about a field of view which is centered on the Y axis gradient field. FIGS. 13(a) through 13(e) are helpful in visualizing the problem. In these FIGURES, the region of interest generating the spin echo signal is assumed to be the entire triangular shape depicted. The center line of the Y-axis gradient field is depicted by a dotted center line notation and the resulting displayed image is also depicted in a box representing the reconstructed field of view. At FIG. 13(a), the triangle is properly centered within the reconstructed and displayed field of view. However, as the triangle moves upwardly with respect to the $G_y$ center line, it will be seen that the reconstructed and displayed image wraps the triangle around by corresponding amounts. When it is located exactly at the top of the field of view in FIG. 13(d), the reconstructed image again appears normally as in FIG. 13(a). Further upward relative motion of the region of interest with respect to the Y axis gradient again produces the same type of wrap around effect as shown in FIG. 13(e) due to the aliasing problem.

One illustrative computer program for performing the necessary scrolling or unwrapping function is depicted diagrammatically at FIG. 17 in flow chart form. If the center line of the region of interest coincides with the center line of a Y axis gradient $G_y$ as tested at block 1700, then an exit back to other programmed processes is made at 1702 since no scrolling action is required. However, if the center line of the region of interest is depicted as being above the gradient center line at 1704, then a remapping function is performed at 1706 so as to scroll or remap the computed pixel values upwardly on a display line by display line basis (with each overflow line from the top being mapped to the bottom of the image so as to begin its upward journey through the remainder of the scrolling function). On the other hand, if the magnetic gradient center line is less than the center line of the region of interest, then the computed pixel values are at 1708 remapped on a display line by display line basis downwardly (with each overflow line from the bottom being remapped to the top of the image to begin its downward movement through the remainder of the scrolling function) as depicted at block 1708.

The earlier discussed two dimensional reconstruction techniques may also be extended to three dimensions. For example, planar regions may also be reconstructed using three dimensional reconstruction techniques. As shown in FIG. 5, the spin echo signal is assumed to emanate from a planar volume. It has already been shown that a two dimensional reconstruction process can be used to resolve the resultant NMR response signals (having improved signal to noise ratio) into an image of the point by point spin density throughout the planar volume. If the planar volume is assumed to be relatively thick as depicted in FIG. 15, three dimensional reconstruction techniques can be similarly applied so as to first effectively resolve the resulting reconstructed spatial distribution of nuclear spin densities into a number of thinner planes—while still achieving the additional signal to noise advantage proportional to the increased time spent in collecting projections in the third dimension.

FIG. 16 depicts a typical exemplary magnetic gradient and r.f. nutation pulse sequence for an elementary measurement cycle that might be used for subdividing a relatively thick planar volume into four thinner planes as illustrated in FIG. 15 using a three dimensional reconstruction Fourier transformation technique. For the Z axis projection "0", the signal sequence illustrated is exactly the same as shown in FIG. 7 except that the value of the Z axis gradient pulses (and/or the frequency spectrum of the nutation pulses) is chosen so as to select the desired relatively thicker planar volume out of the object for irradiation by the 90° and 180° nutation pulses. In this projection "0" the negative rephasing or phase encoding pulse in the Z axis direction just following the 90° r.f. nutation pulse is of nominal value as depicted in FIG. 16. After one complete overall sequence of measurement cycles for projection "0", an additional entire sequence is then taken with a Z-axis directed phase encoding for another projection (e.g. "+1"). To produce Z axis directed phase encoding, one could add an additional Z axis gradient pulse between the 90° and 180° nutation pulses.

Alternatively, the presently preferred exemplary embodiment, as illustrated, uses a somewhat more simple approach. The negative rephasing $G_z$ gradient is simply modified by an amount which provides the desired Z-axis phase encoding. In the illustrated example, the "+2" projection has sufficiently positive encoding added so that the negative phasing pulse is, in fact, a positive gradient pulse rather than negative. For each such Z-axis projection, an entire set of Y-axis phase encodings using all of the different $G_y$ gradient values is taken.

As with the rapid multiple plane imaging technique, the illustrated technique does not require the 4-phased averaging technique to cancel interfering residual FID signals since there should be no such interfering signals where the same subvolumes are excited by both the 90° and 180° nutation pulses. Consequently, one might be able to reduce the number of spin echo signals that are averaged together before the three dimensional Fourier transform reconstruction process is undertaken in favor of a substituted number of projections in the third or Z axis dimension.

If the Z axis dimension in this case is four times as thick, then one may image four times as many planes with the same signal to noise ratio. This is so because the four projections improve the signal to noise ratio in the same way that the four averaged spin echo signals do in the two dimensional embodiments.

Another alternative is to use the same relatively thinner planar regions for deriving spin echo NMR signals but then using the three dimensional reconstruction technique to resolve the resulting reconstruction into planar volumes that are effectively four times as thin thus gaining an effectively greater resolution capability. (In this latter case, one would lose signal to noise ratio by a factor of 4 due to the one-fourth thinner slice volume.)

One advantage of the planar region three dimensional reconstruction technique over the straightforward use of rapid multiple plane imaging is where a gated imaging of a moving element (e.g. a moving beating heart) is contemplated. Here, if a multiple rapid plane data gathering sequence (e.g. a time/spatial division multiplexing technique) is used in a region which includes a beating heart, the first slice NMR signal responses may occur at a desired gate time. However, subsequently generated NMR spin echo signals from subsequent slices within the same spin-lattice relaxation time T1 will necessarily occur at progressively later times in the cardiac cycle.

This may well be undesirable where a physician typically wants to see all of the heart images at a common time in the cardiac cycle. Although one could repeat the multiple slice procedure with a different slice being the first one in time so as to obtain a similar end result, this would require as many repetitions of the imaging procedure as there are slices—a very time-consuming approach which effectively eliminates the time/spatial division multiplexing advantages.

Using a three-dimensional reconstruction technique within a relatively thick planar region centered over the heart, all of the NMR signal response data used to reconstruct the images may be collected at the same relative times in the cardiac cycle. Accordingly, all of the reconstructed planar images will represent the same relative point in the cardiac cycle. Of course, the total imaging time required will be increased by the number of desired projections used in the three-dimensional reconstruction technique so as to obtain the required number of reconstructed planar images, one will still get a signal-to-noise improvement from the extra signal capturing time involved in the process. If the number of averaged spin echo signals can be reduced, one could trade-off the improved signal-to-noise ratio for shorter imaging time.

Three-dimensional reconstructions do require more computer storage and processing apparatus and time than two-dimensional reconstruction processes. However, by using three-dimensional reconstruction processes in conjunction with only a relatively small selected sub-volume of the entire object, the relatively smaller number of projections required to sub-divide the relatively thick planar region makes this an attractive alternative as compared to a full three-dimensional reconstruction throughout the entire object.

In the three-dimensional reconstruction case one can combine both multiple angle and Fourier imaging techniques. For example the two dimensions in the plane can be reconstructed from data taken as multiple angle projections where the planes are defined by phase encoding in the z direction and are reconstructed by Fourier transformation.

Just as in the sub-planar region and two-dimensional reconstruction techniques already described, a sub-volume region of interest can be defined to produce NMR spin echo signals from what can be considered as a "tall" and/or "thick" line volume. A three-dimensional reconstruction process can just as well be imposed on this type of data to sub-divide it into both lines and/or planes and thus to obtain an image of the region of interest containing plural planar images of nuclear spin density all acquired from spin echo data taken at the same time. As earlier described, this may be of significant utility when a time-gated signal taking sequence is desired within the region of interest so as to effectively "freeze" a moving element (e.g., a beating heart) at some particular point in its cyclic motion. The residual FID interference problem can be expected to be the same as for two-dimensional regions of interest so that the same motion artifact considerations apply. Namely, four differently phased sets of nutation pulses are preferred together with special averages of the resulting NMR spin echo signals before the reconstruction process is applied. The additional adjacent sub-volume regions which lie on a "diagonal" are probably outside the region of interest so that one effectively can be expected to lose the otherwise possible time/spatial division multiplex advantages.

Table 1, shown below, summarizes the expected relative imaging times and signal-to-noise ratios for NMR imaging techniques ranging from techniques using point-by-point to full three-dimensional reconstructions of the entire object. In Table 1, the time required for nuclei to return to equilibrim between measurements is denoted by T, the number of regions which can be measured within time T (when multiple regions can be sequentially imaged in this way) is m and the signal-to-noise ratio for a single measurement is assumed to be one (1). In the case where planar volume regions are sub-divided by three-dimensional reconstruction techniques, the number of sub-divisions is denoted by s. The displayed pixel sizes are all assumed to be of equal size.

TABLE 1

|  | Single point image | | Line image | | Single plane image | | m plane image | | ms plane image | | full vol. of N planes | |
| --- | --- | --- | --- | --- | --- | --- | --- | --- | --- | --- | --- | --- |
|  | Time | S/N | Time | S/N | Time | S/N | Time | S/N | Time | S/N | Time | S/N |
| point-by-point | T | 1 | NT | 1 | $N^2T$ | 1 | $mN^2T$ | 1 | $msN^2T$ | 1 | $N^3T$ | 1 |
| line-by-line | T | 1 | T | 1 | NT | 1 | mNT | 1 | msNT | 1 | $N^2T$ | 1 |
| rapid multiple planes | NT | $\sqrt{N}$ | NT | $\sqrt{N}$ | NT | $\sqrt{N}$ | NT | $\sqrt{N}$ | sNT | $\sqrt{N}$ | $\frac{N^2}{m}T$ | $\sqrt{N}$ |
| rapid multiple planar regions sub-divided by 3-D reconstruction | sNT | $\sqrt{sN}$ | sNT | $\sqrt{sN}$ | sNT | $\sqrt{sN}$ | sNT | $\sqrt{sN}$ | sNT | $\sqrt{sN}$ | $\frac{N^2}{m}T$ | $\sqrt{sN}$ |
| full 3-D reconstruction | $N^2T$ | N | $N^2T$ | N | $N^2T$ | N | $N^2T$ | N | $N^2T$ | N | $N^2T$ | N |

Observing the entries in Table 1, one can appreciate an example of the potential advantage of sub-dividing multiple regions. For example, if one wants to image ms planes, there are at least two possible approaches. The rapid multiple plane imaging technique (time/spatial division multiplexing) can be applied to image the first m planes of the ms planes after which the next m planes are similarly imaged and so on until all ms planes have been imaged. The total time required is sNT and the signal-to-noise ratio is the square root of N. On the other hand, if instead, m regions are sub-divided into s planes using three-dimensional reconstruction techniques as described above, the total imaging time will still be sNT but the signal-to-noise ratio will now be the square root of sN. That is, the signal-to-noise ratio has been improved by a factor of the square root of s times.

While only a few specific exemplary embodiments of this invention have been described in detail, those skilled in the art will appreciate that many modifications and variations of this embodiment may be made without departing from the novel and advantageous features of this invention. Accordingly, all such variations and modifications are intended to be included within the scope of the appended claims.

What is claimed is:

1. A method of generating multi-dimensional NMR signals for use in deriving an image of the point-by-point spatial distribution of related nuclei within a selected portion of an object, said method comprising the steps of:
   (a) selectively nutating nuclei in only a predetermined sub-volume of the object to elicit an NMR spin echo response therefrom;
   (b) repeating step (a) for plural other different sub-volumes during a single T1 spin-lattice relaxation time period; and
   (c) reconstructing a point-by-point distribution of nutated nuclei within each said subvolume using a multi-dimensional reconstruction process based on the NMR spin echo signals emanating therefrom.

2. A method as in claim 1 wherein said multi-dimensional reconstruction process comprises a two-dimensional Fourier transformation of said spin echo signals.

3. A method as in claim 1 wherein said multi-dimensional reconstruction process comprises a three-dimensional Fourier transformation of said spin echo signals.

4. A method as in claim 1 wherein said multi-dimensional reconstruction process comprises a Fourier transformation of said spin echo signals to provide projections from multiple angles which are then processed by filtered back projection.

5. A method of generating multi-dimensional NMR signals, said method comprising the steps of:
   (a) selectively nutating the nuclei in a first sub-volume of an object with a predetermined r.f. nutation pulse;
   (b) thereafter subjecting said object to a predetermined nuclei de-phasing magnetic field gradient to thus correspondingly phase-encode the just nutated nuclei;
   (c) selectively nutating the nuclei in at least a portion of said first sub-volume with a 180° r.f. nutation pulse;
   (d) measuring the resulting first NMR spin echo signal emanating from said portion while subjecting said object to a predetermined magnetic field gradient;
   (e) again selectively nutating the nuclei in at least a portion of said first sub-volume with a 180° r.f. nutation pulse;
   (f) measuring the resulitng second NMR spin echo signal emanating from said portion while subjecting said object to a predetermined magnetic field gradient;
   (g) repeating steps (a)–(f) for each of different other sub-volumes of the object during the spin-lattice relaxation time T1 of the nuclei in said first sub-volume; and
   (h) repeating steps (a)–(g) using different predetermined nuclei de-phasing magnetic fields in step (b) to thus generate a corresponding set of plural measured first and second NMR spin echo signals as said multi-dimensional NMR signals.

6. A method as in claim 5 further comprising the step of:
   (i) repeating steps (e)–(f) to measure a third and a predetermined number of subsequent spin echoes each with less signal intensity due to T2 decay.

7. A method as in claim 5 further comprising:
   (i) repeating steps (a)–(f) for each sub-volume using the same predetermined de-phasing magnetic field and with the resulting measured similar NMR spin echo signals being respectively accumulated to provide averaged NMR spin echo signals of enhanced signal-to-noise ratio.

8. A method as in claim 7 further comprising the step of:
   (j) reconstructing an image of point-by-point spatial distribution of nutated nuclei density within at least one said sub-volume by Fourier transforming said averaged NMR spin echo signals to provide plural one-dimensional density projections thereof from different angular orientations which are then converted to an array of pixel value data signals representing said image.

9. A method as in claim 7 further comprising the step of:
   (j) reconstructing an image of point-by-point spatial distribution of nutated nuclei density within at least one said sub-volume by two-dimensionally Fourier transforming said averaged NMR spin echo signals to generate an array of pixel value data signals representing said image.

10. A method as in claim 7 further comprising:
   (j) repeating steps (a)–(i) using different predetermined magnetic field gradients during the nuclei dephasing and measurement steps to thus generate corresponding further sets of averaged NMR spin echo signals encoded in a third dimension; and
   (k) reconstructing an image of point-by-point spatial distribution of nutated nuclei density within at least one said sub-volume by three-dimensionally Fourier transforming said averaged NMR spin echo signals to generate an array of pixel value data signals representing said image.

11. A method as in claim 5, 6, 7, 8, 9 or 10 wherein at least one of said selective nutating steps (a) and, (c) and (e) substantially avoids relatively moving elements within said object.

12. A method as in claim 5, 6, 7, 8, 9 or 10 wherein said selective nutating steps (a), (c) and (e) stubstantially avoid relatively moving elements within said object.

13. A method as in claim 9 wherein the centerline of the reconstructed field of view is non-coincident with the centerline of the de-phasing magnetic field gradient used in step (b) and further comprising the step of:
   (k) reordering the lines of pixel value data signals prior to visual display thereof to compensate for aliasing caused by said non-coincident centerlines.

14. A method of NMR imaging wherein electrical signals representing the relative spatial distribution of nuclei density within a predetermined volume of an object are generated and made available for use in a visual display, said method comprising the steps of:
   (a) selectively exciting the nuclei within said predetermined volume of the object to generate at least one first NMR spin echo response signal by successively applying a 90° r.f. nutation and at least one 180° r.f. nutation pulse of r.f. energy to selected first and second volumes of the object which intersect in said predetermined volume, wherein a predetermined relative NMR phase encoding magnetic field gradient is also applied to the object between said 90° and 180° nutation pulses;

(b) recording data representing said at least one first NMR spin echo response;

(c) repeating said selective excitation and recording steps (a) and (b) to generate averaged NMR spin echo responses from the intersecting volume for said predetermined phase encoding;

(d) repeating steps (a), (b) and (c) for different predetermined phase encoding thus generating plural corresponding averaged NMR spin echo responses; and (e) reconstructing an array of signals representing said relative spatial density distribution within said predetermined volume using said plurality of averaged NMR spin echo responses.

15. A method as in claim 14 wherein said first and second intersecting volumes are substantially coplanar volumes.

16. A method as in claim 14 wherein said first and second intersecting volumes are substantially non-coplanar.

17. A method as in claim 16 wherein said object includes predetermined portions undergoing relative motion and wherein neither said first nor second intersecting volumes also intersect said predetermined portion.

18. A method as in claim 14, 15, 16 or 17 wherein a measure of the spatial distribution of nuclei density is derived by a two-dimensional Fourier transformation of said averaged NMR spin echo responses.

19. A method as in claim 14, 15, 16, or 17 wherein a measure of the spatial distribution of nuclei density is derived by reconstruction of one-dimensional density projections taken at different relative angular orientations as represented by said averaged NMR spin echo responses.

20. A method as in claim 14 wherein steps (a)-(d) are further repeated plural times during each of which further repetitions a different predetermined further phase-encoding magnetic field is employed in a direction transverse to the first-mentioned phase-encoding fields so as to provide plural further sets of averaged NMR spin echo responses representing encoded nuclei densities along a third dimension.

21. A method as in claim 20 wherein a measure of the spatial distribution of nuclei density throughout a three-dimensional region of the object is derived by a three-dimensional Fourier transformation of said averaged NMR spin echo responses.

22. A method of NMR imaging wherein electrical signals representing the relative spatial density distribution of nuclei within predetermined planar volumes of an object are generated and made available for use in a visual display, said method comprising the steps of:

(a) selectively exciting nuclei within a first predetermined planar volume of said object to generate at least one first NMR spin echo response signal by successively applying a 90° and at least one 180° nuclei nutation pulses of r.f. energy to substantially coplanar volumes of the object under a predetermined relative NMR phasing environment;

(b) recording said at least one first NMR spin echo response;

(c) repeating said selective excitation and recording steps (a) and (b) for other different planar volumes within said object during the T1 NMR relaxation time of said nuclei occurring after step (a);

(d) thereafter repeating steps (a), (b) and (c) to generate averaged NMR spin echo responses for each of the predetermined planar volumes;

(e) also thereafter repeating steps (a)-(d) for different predetermined relative NMR phasing environments so as to generate a corresponding plurality of averaged NMR spin echo responses for each predetermined planar volume; and reconstructing an array of signals representing said relative spatial density distribution within each of said planar volumes using said plurality of averaged NMR spin echo responses from that plane.

23. A method as in claim 22 wherein said reconstructing step includes:

Fourier transformation of each averaged spin echo responses to obtain one-dimensional nuclei density projections at each of different relative angular orientations; and reconstruction of said spatial density distribution using said one-dimensional projections.

24. A method as in claim 22 wherein said reconstruction step includes:

a first Fourier transformation of each averaged spin echo response to obtain a plurality of one-dimensional nuclei density projections for each said planar volume along a first dimension; and a second Fourier transformation of signal values taken from said one-dimensional density projections along a second column dimension transverse to said first dimension for each said planar volume to provide an array of elemental pixel value signals representing the desired spatial density distribution along said second column dimension.

25. A method as in claim 24 wherein the centerline of a field-of-view used in the reconstruction step is not aligned with the center of a vertical magnetic gradient field used for phase-encoding in the portion of the object generating said spin echo responses thus causing a wraparound aliasing problem and further comprising the step of unwrapping the reconstructed data for display purposes by re-arranging the vertical line-order of the array of signals to be visually displayed.

26. Apparatus for generating multi-dimensional NMR signals for use in deriving an image of the point-by-point spatial distribution of nutated nuclei within a selected portion of an object, said apparatus comprising:

(a) means for selectively nutating nuclei in only a predetermined sub-volume of the object to elicit an NMR spin echo response therefrom;

(b) means for repeating step (a) for plural other different subvolumes during a single T1 spin-lattice relaxation time period; and (c) means for reconstructing a point-by-point distribution of nutated nuclei within each said sub-volume using a multi-dimensional reconstruction process based on the NMR spin echo signals emanating therefrom.

27. Apparatus as in claim 26 wherein said means for reconstructing comprises means for performing a two-dimensional Fourier transformation of said spin echo signals.

28. Apparatus as in claim 26 wherein said means for reconstructing comprises means for performing a three-dimensional Fourier transformation of said spin echo signals.

29. Apparatus for generating multi-dimensional NMR signals, said apparatus comprising:

(a) means for selectively nutating the nuclei in a first sub-volume of an object with a predetermined r.f. nutation pulse;
(b) means for thereafter subjecting said object to a predetermined nuclei de-phasing magnetic field gradient to thus correspondingly phase-encode the just nutated nuclei;
(c) means for selectively nutating the nuclei in at least a portion of said first sub-volume with a 180° r.f. nuclei pulse;
(d) means for measuring the resulting first NMR spin echo signal emanating from said portion while subjecting said object to a predetermined magnetic field gradient;
(e) means for again selectively nutating the nuclei in at least a portion of said first sub-volume with a 180° r.f. nutation pulse;
(f) means for measuring the resulting second NMR spin echo signal emanating from said portion while subjecting said object to a predetermined magnetic field gradient;
(g) means for repetitively operating means (a)–(f) for each of different other sub-volumes of the object during the spin-lattice relaxation time T1 of the nuclei in said first sub-volume; and
(h) means for repetitively operating means (a)–(f) using different predetermined nuclei de-phasing magnetic fields in means (b) to thus generate a corresponding set of plural measured first and second NMR spin echo signals as said multi-dimensional NMR signals.

30. Apparatus as in claim 29 or 31 further comprising:
(i) means for repetitively operating means (a)–(f) for each sub-volume using the same predetermined de-phasing magnetic field and with the resulting measured similar NMR spin echo signals being respectively accumulated to provide averaged NMR spin echo signals of enhanced signal-to-noise ratio.

31. Apparatus as in claim 30 further comprising:
(j) means for reconstructing an image of point-by-point spatial distribution of nutated nuclei density within at least one said sub-volume by Fourier transforming said averaged NMR spin echo signals to provide plural one-dimensional density projections thereof from different angular orientations which are then converted to an array of pixel value data signals representing said image.

32. Apparatus as in claim 30 further comprising:
(j) means for reconstructing an image of point-by-point spatial distribution of nutated nuclei density within at least one said sub-volume by two-dimensionally Fourier transforming said averaged NMR spin echo signals to generate an array of pixel value data signals representing said image.

33. Apparatus as in claim 30 further comprising:
(j) means for repetitively operating means (a)–(i) using different predetermined magnetic field gradients during the nuclei dephasing steps to thus generate corresponding further sets of averaged NMR spin echo signals encoded in a third dimension; and
(k) means for reconstructing an image of point-by-point spatial distribution of nutated nuclei density within at least one said sub-volume by three-dimensionally Fourier transforming said averaged NMR spin echo signals to generate an array of pixel value data signals representing said image.

34. Apparatus as in claim 29 wherein at least one of said means (a), (c) or (e) substantially avoids nutating nuclei within relatively moving elements within said object.

35. Apparatus as in claim 29 wherein said means (a), (c) and (e) substantially avoid nutating nuclei within relatively moving elements within said object.

36. Apparatus as in claim 32 wherein the centerline of the reconstructed field of view is non-coincident with the centerline of the de-phasing magnetic field gradient used in means (b) and further comprising:
(k) means for reordering the lines of pixel value data signals prior to visual display thereof to compensate for aliasing caused by said non-coincident centerlines.

* * * * *

UNITED STATES PATENT AND TRADEMARK OFFICE
CERTIFICATE OF CORRECTION

PATENT NO. : 4,599,565
DATED : July 8, 1986
INVENTOR(S) : John Hoenninger; Lawrence Crooks & Mitsuaki Arakawa It is certified that error appears in the above-identified patent and that said Letters Patent is hereby corrected as shown below:

<u>Cover Sheet</u>, Page 1, column 2 under "OTHER PUBLICATIONS", line 1, change "Phip." to --Phis.--;
line 4, change "Nes" to --Res--; and
line 7, change "Phip." to --Phis.--.

<u>Cover Sheet</u>, Page 2, column 2, line 2, change "Couput" to --Comput--.

<u>Column 33</u>, line 32, delete "or 31".

Signed and Sealed this

Twenty-third Day of September 1986

[SEAL]

Attest:

DONALD J. QUIGG

Attesting Officer     Commissioner of Patents and Trademarks